US011076971B2

United States Patent
Endo et al.

(10) Patent No.: US 11,076,971 B2
(45) Date of Patent: Aug. 3, 2021

(54) ACTUATOR AND ARTIFICIAL LEG

(71) Applicant: Sony Corporation, Tokyo (JP)

(72) Inventors: Ken Endo, Shinagawa-ku (JP); Hirozumi Takeshima, Shinagawa-ku (JP)

(73) Assignee: SONY CORPORATION, Tokyo (JP)

( * ) Notice: Subject to any disclaimer, the term of this patent is extended or adjusted under 35 U.S.C. 154(b) by 210 days.

(21) Appl. No.: 16/098,867

(22) PCT Filed: Mar. 2, 2017

(86) PCT No.: PCT/JP2017/008329
§ 371 (c)(1),
(2) Date: Nov. 5, 2018

(87) PCT Pub. No.: WO2017/212708
PCT Pub. Date: Dec. 14, 2017

(65) Prior Publication Data
US 2019/0142612 A1     May 16, 2019

(30) Foreign Application Priority Data

Jun. 7, 2016   (JP) .............................. JP2016-113847

(51) Int. Cl.
*A61F 2/70*     (2006.01)
*A61F 2/64*     (2006.01)
(Continued)

(52) U.S. Cl.
CPC .................. *A61F 2/70* (2013.01); *A61F 2/64* (2013.01); *B25J 9/10* (2013.01); *B25J 19/00* (2013.01);
(Continued)

(58) Field of Classification Search
CPC ........ A61F 2/64; A61F 2/70; A61F 2002/741; A61F 2002/744; B25J 9/0015; F16F 1/14;
(Continued)

(56) References Cited

U.S. PATENT DOCUMENTS 3,672,797 A * 6/1972 Gerlach et al. ......... F01C 1/344
418/125
4,412,794 A * 11/1983 Presley .................. H02K 41/06
310/82

(Continued)

FOREIGN PATENT DOCUMENTS

FR        556363 A      7/1923
JP     S35-30606 Y1    11/1960

(Continued)

OTHER PUBLICATIONS

Otani, T. et al., "Development of Biped Running Robot Utilizing Pelvic Movement (Dai 11 Ho: CFRP Kasane Itabane ni yoru Keiryo Koshutsuryoku Dansei Kansetsu Kiko)," The 33rd Annual Conference of the Robotics Society of Japan Yokoshu DVD-ROM, Sep. 3, 2015 (Sep. 3, 2015), RSJ2015AC3I-04, pp. 1-10 (See English-language Translation).

(Continued)

*Primary Examiner* — Christopher P Schwartz
(74) *Attorney, Agent, or Firm* — Xsensus LLP

(57) ABSTRACT

To propose a novel and improved actuator and artificial leg capable of miniaturizing an apparatus.

An actuator (320) includes: a leaf spring (322) whose one end (322a) is cantilevered, the leaf spring being capable of deflection deformation in a plate thickness direction in accordance with torque by transmitting the torque; and a support member (324) configured to support a part of the (Continued)

leaf spring on a deflection direction side in a case where the torque transmitted by the leaf spring is greater than a predetermined value.

10 Claims, 13 Drawing Sheets

(51) Int. Cl.
 *B25J 19/00* (2006.01)
 *B25J 9/10* (2006.01)
 *H02K 7/14* (2006.01)
 *A61F 2/50* (2006.01)
 *A61F 2/74* (2006.01)
(52) U.S. Cl.
 CPC ........ *H02K 7/14* (2013.01); *A61F 2002/5079* (2013.01); *A61F 2002/741* (2013.01)
(58) Field of Classification Search
 CPC ...... F16F 1/145; F16F 1/18; F16F 1/22; F16F 1/26; F16F 1/322; F16D 3/56
 USPC .............. 267/158–165; 192/54.5; 602/16, 26
 See application file for complete search history.

(56) References Cited

U.S. PATENT DOCUMENTS

| | | | |
|---|---|---|---|
| 8,696,764 B2* | 4/2014 | Hansen | A61F 2/6607 623/52 |
| 9,206,688 B2* | 12/2015 | Landrum | F01C 21/0881 |
| 9,376,036 B2* | 6/2016 | Wei | B60N 2/236 |
| 10,364,858 B2* | 7/2019 | Knoll | B25J 17/0225 |
| 10,626,944 B2* | 4/2020 | Liao | F16F 1/3821 |
| 2014/0001006 A1 | 1/2014 | Liermann | |
| 2015/0051528 A1* | 2/2015 | Gilbert | F16D 65/065 602/16 |
| 2019/0126498 A1* | 5/2019 | Schimmels | F16F 1/22 |
| 2020/0298426 A1* | 9/2020 | Ayuzawa | B25J 9/0012 |

FOREIGN PATENT DOCUMENTS

| | | |
|---|---|---|
| JP | S54-133249 A | 10/1979 |
| JP | S59-32452 A | 2/1984 |
| JP | 2002-332871 A | 11/2002 |
| JP | 2010-139067 A | 6/2010 |
| JP | 2014-021741 A | 2/2014 |
| JP | 2014-140300 A | 7/2014 |
| JP | 2014-144037 A | 8/2014 |

OTHER PUBLICATIONS

Takeshima, H. et al., "Leaf Spring with a Deform guide for the Torque Sensor," The Proceedings of JSME Annual Conference on Robotics and Mechatronics 2016, Jun. 8, 2016 (Jun. 8, 2016), 2PI-13b3, pp. 1-9 (See English-language Translation).
English-language Translation of International Search Report and Written Opinion for International Application No. PCT/JP2017/008329, dated May 23, 2017.

* cited by examiner

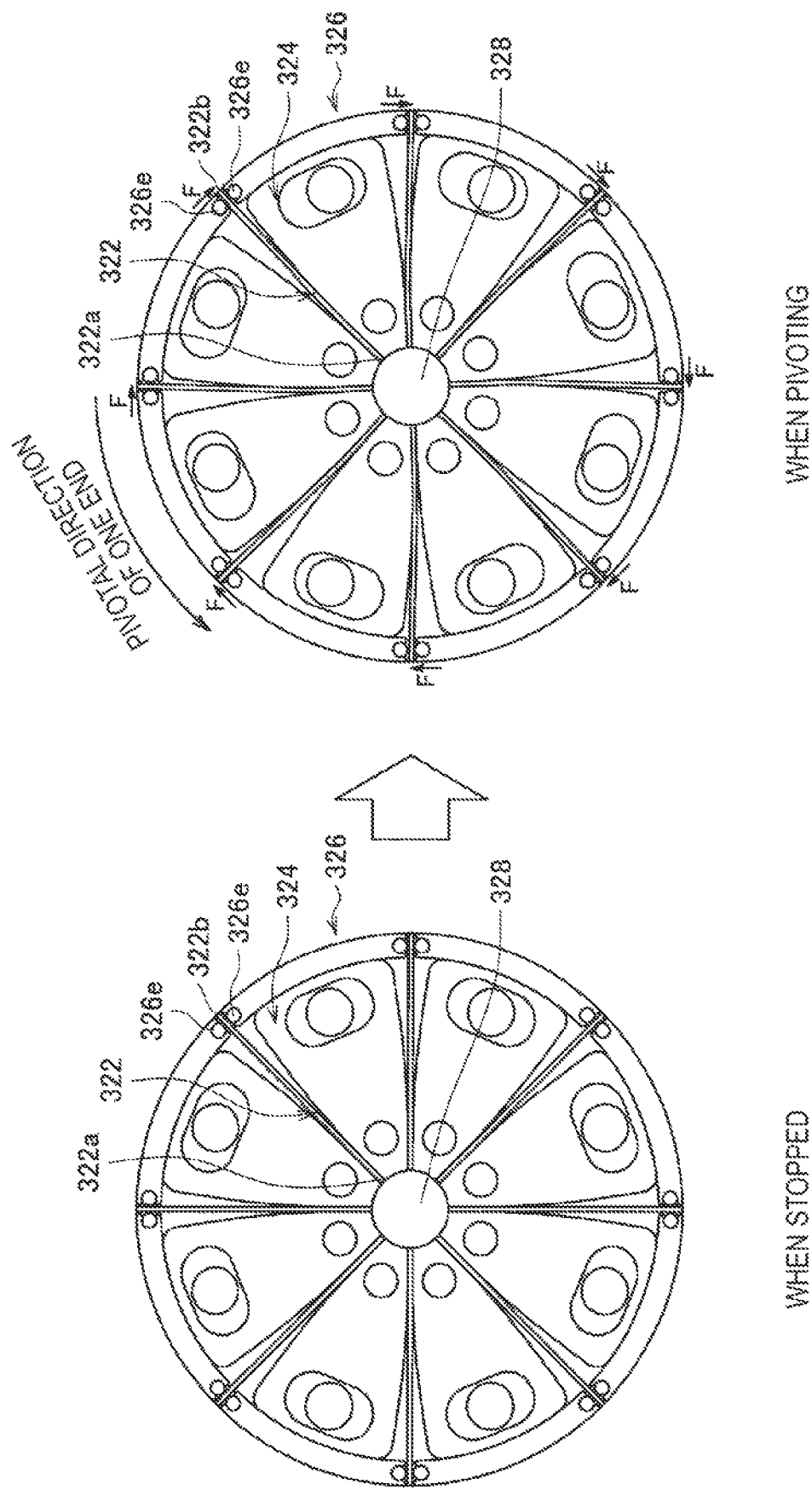

ACTUATOR AND ARTIFICIAL LEG

CROSS-REFERENCE TO RELATED APPLICATIONS

This application is a National Stage Application based on PCT/JP2017/008329, filed 2 Mar. 2017, and claims priority to Japanese Patent Application No, 2016-113847 on 7 Jun. 2016, the entire contents of which being incorporated herein by reference.

TECHNICAL FIELD

The present disclosure relates to an actuator and an artificial leg.

BACKGROUND ART

In recent years, to achieve desired drive control for each apparatus, there have been proposed a variety of actuators. Specifically, to achieve drive control required for a robot that is an apparatus modeled after a human shape and movement, there is proposed a series elastic actuator referred to as series elastic actuator (SEA) (see, for example, Patent Literature 1 and the like).

CITATION LIST

Patent Literature

Patent Literature 1: JP 2014-140300A

DISCLOSURE OF INVENTION

Technical Problem

Incidentally, it is desired in the field related to robots to make apparatuses smaller. Here, it is expected to miniaturize an apparatus by miniaturizing an SEA used as an actuator of a robot. However, the SEA specifically transmits power via a spring serving as an elastic member. Accordingly, in the case where the SEA is miniaturized, it can be necessary to miniaturize the spring in the SEA. This causes the strength of the spring to be less than required strength in some cases. Therefore, it can be difficult to miniaturize the SEA.

Then, the present disclosure proposes a novel and improved actuator and artificial leg capable of miniaturizing an apparatus.

Solution to Problem

According to the present disclosure, there is provided an actuator including: a leaf spring whose one end is cantilevered, the leaf spring being capable of deflection deformation in a plate thickness direction in accordance with torque by transmitting the torque; and a support member configured to support a part of the leaf spring on a deflection direction side in a case where the torque transmitted by the leaf spring is greater than a predetermined value.

In addition, according to the present disclosure, there is provided an artificial leg including a thigh side member; a lower leg side member; and an actuator configured to connect the thigh side member to the lower leg side member, and transmit torque to the lower leg side member to relatively pivot the lower leg side member with respect to the thigh side member. The actuator includes a leaf spring whose one end is cantilevered, the leaf spring being capable of deflection deformation in a plate thickness direction in accordance with torque by transmitting the torque, and a support member configured to support a part of the leaf spring on a deflection direction side in a case where the torque transmitted by the leaf spring is greater than a predetermined value.

Advantageous Effects of Invention

According to the present disclosure as described above, it is possible to miniaturize an apparatus.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 17 is a schematic diagram illustrating an example of a condition of the actuator according to the embodiment in a case where the one end of the leaf spring is relatively stopped with respect to a pivotal object and in a case where the one end of the leaf spring pivots with respect to the pivotal object.

MODE(S) FOR CARRYING OUT THE INVENTION

Figure 1:
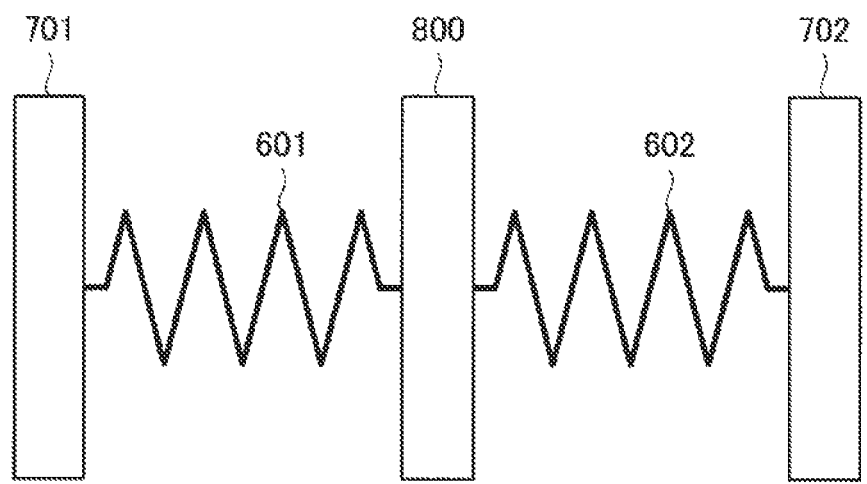
FIG. 1 is an explanatory diagram for describing compliance control by an SEA.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. Overview of Series Elastic Actuator
2. Artificial Leg according to Embodiment of the Present Disclosure
3. Overview of the Present Technology
3-1. Deformation of Leaf Spring
3-2. Mechanical Characteristic of Leaf Spring
4. Actuator according to Embodiment of the Present Disclosure
5. Conclusion

1. OVERVIEW OF SERIES ELASTIC ACTUATOR

As described above, as an actuator for driving a robot, an SEA is used. The SEA specifically transmits power output from a drive motor to a target object on an output side via a spring serving as an elastic member. Configured in this way, the SEA has higher compliance than that of another actuator. Accordingly, it is possible to reduce impact applied to an apparatus including the SEA. With this arrangement, the use of the SEA for a joint section of the robot makes it possible to reduce impact from the ground contact area in the case where the robot performs a landing operation or the like.

In addition, the SEA can measure a load applied to a spring on the basis of a measurement value of the displacement amount of the spring and a spring constant of the spring. The load measured in this way is relevant to power actually transmitted to a target object on the output side, so that it is possible to use a measurement result of the load for drive control over the SEA. Here, to measure a load applied to an object, the measurement of force with a strain gauge is widely used. However, the measurement of force with a strain gauge easily results in low measurement accuracy because of influence of noise of an electrical signal processed in the measurement in the case where the load applied to an object is relatively small. Meanwhile, when a load is measured with a measurement value of the displacement amount of a spring, it is possible to secure relatively high measurement accuracy irrespective of the degree of the load applied to the spring. Therefore, when a load is measured with a measurement value of the displacement amount of a spring, it is possible to improve measurement accuracy as compared with the measurement of force with a strain gauge even in the case where the load of the measurement target is relatively small.

The use of the characteristic of the SEA described above makes it possible to achieve drive control required for a robot that is an apparatus modeled after a human shape and movement. Specifically, the SEA can measure a load applied to a spring with relatively high measurement accuracy even in the case where a load of a measurement target is relatively small. Accordingly, it is possible to more accurately control power transmitted to a target object on the output side. With this arrangement, according to the SEA, for example, it is possible to achieve compliance control over which a target object on the output side is made to move while keeping relatively high compliance.

As an example, with reference to a system including an input side mass object 701, an input side mass object 702, an output side mass object 800, a spring 601, and a spring 602 illustrated in FIG. 1, such compliance control will be described. It is assumed that the SEA includes each component schematically illustrated in FIG. 1. As illustrated in FIG. 1, the output side mass object 800 is positioned between the input side mass object 701 and the input side mass object 702. The input side mass object 701 and the output side mass object 800 are connected via the spring 601. The input side mass object 702 and the output side mass object 800 are connected via the spring 602. In addition, the expansion and contraction directions of the spring 601 and the spring 602 agree with each other. In addition, power output from a drive motor that is not illustrated is configured to be input into the input side mass object 701 and the input side mass object 702, and transmitted to the output side mass object 800 via the spring 601 and the spring 602. Specifically, the power input into the input side mass object 701 and the input side mass object 702 is transmitted to the output side mass object 800 via the spring 601 and the spring 602 by the spring 601 and the spring 602 expanding and contracting. Note that the power transmitted to the output side mass object 800 can be transmitted to a target object connected to the output side mass object 800 which is not illustrated.

In the system illustrated in FIG. 1, the case will be considered where the output side mass object 800 moves along the expansion and contraction directions of the spring 601 and the spring 602. In such a case, adjusting the positions of the input side mass object 701 and the input side mass object 702 along the movement direction of the output side mass object 800 allows the length of the spring 601 and the spring 602 to be adjusted. For example, adjusting the positions of the input side mass object 701 and the input side mass object 702 such that the length of each of the springs 601 and 602 approximates equilibrium length makes it possible to keep relatively low a load that is applied to the output side mass object 800. With this arrangement, it is possible to achieve compliance control over which the output side mass object 800 is made to move while keeping relatively high compliance.

The use of the SEA as an actuator of a robot in this way makes it possible to achieve drive control required for a robot that is an apparatus modeled after a human shape and movement. Here, as described above, it is desired in the field related to robots to make apparatuses smaller. In addition, it is expected to miniaturize an apparatus by miniaturizing an SEA used as an actuator of a robot. However, in the case where the SEA is miniaturized, it can be necessary to miniaturize the spring in the SEA. This causes the strength of the spring to be less than required strength in some cases. Therefore, it can be difficult to miniaturize the SEA. To miniaturize an apparatus including the SEA, the following describes a mechanism for miniaturizing the SEA.

2. ARTIFICIAL LEG ACCORDING TO EMBODIMENT OF THE PRESENT DISCLOSURE

Figure 2:
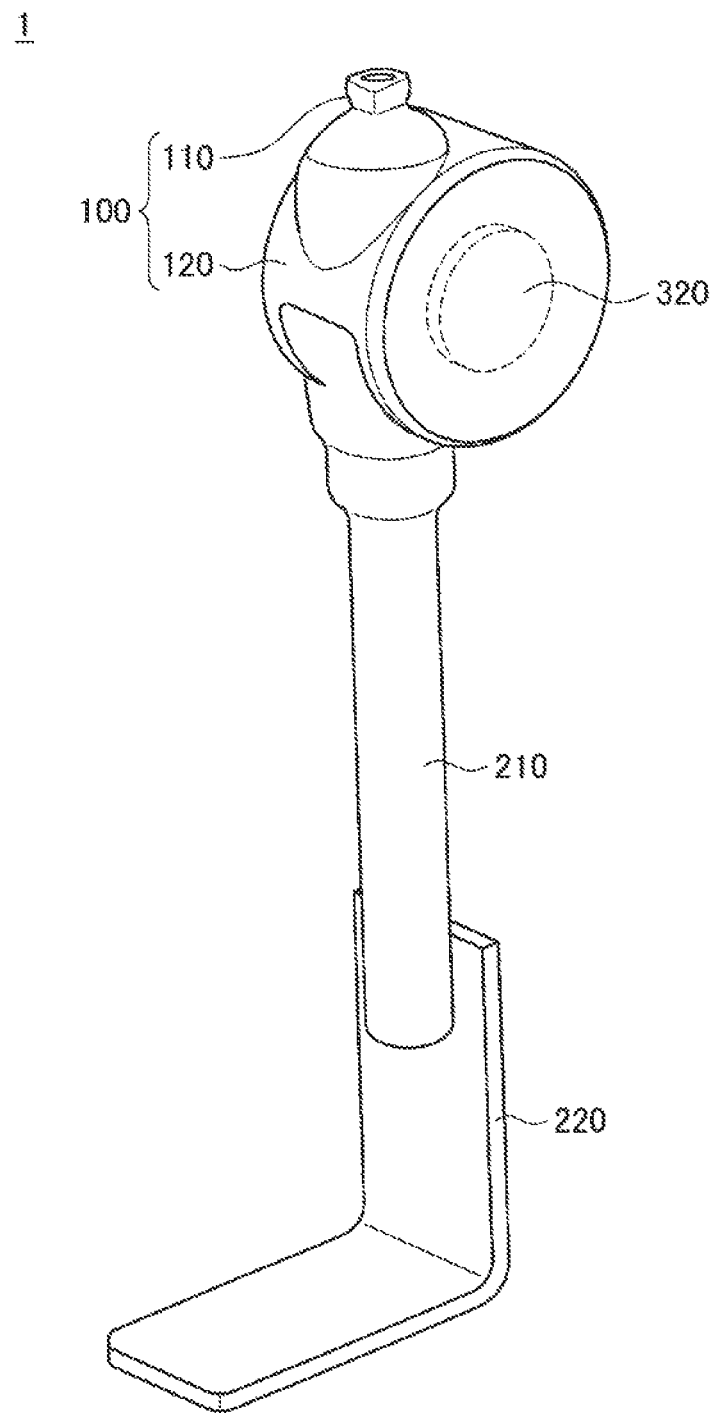
FIG. 2 is a schematic diagram illustrating an example of a schematic configuration of an artificial leg according to an embodiment of the present disclosure.
Figure 3:
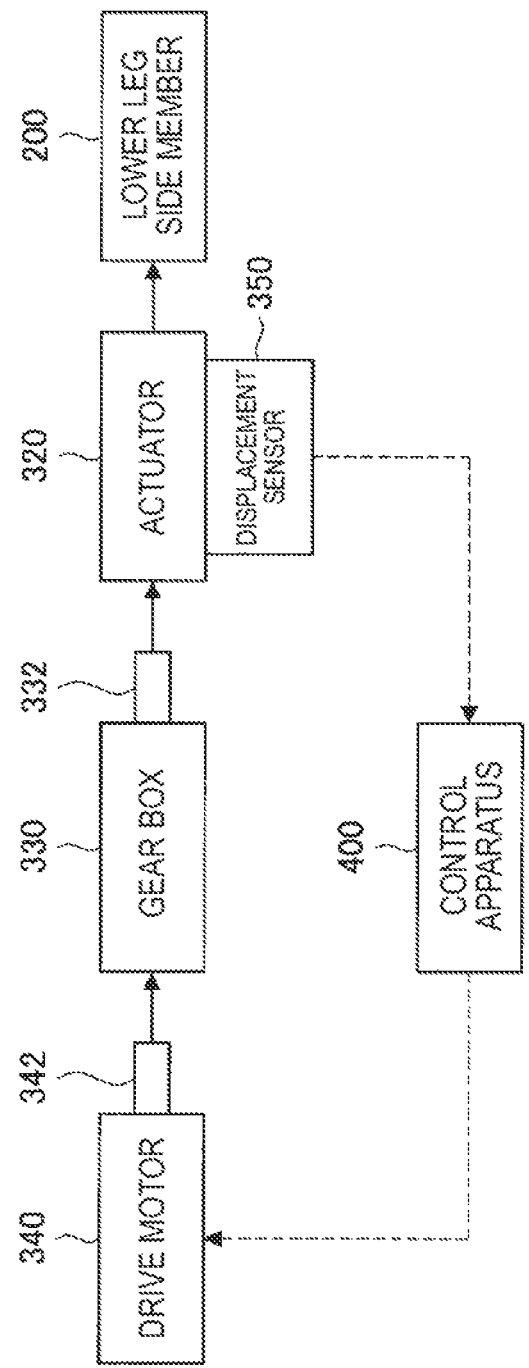
FIG. 3 is an explanatory diagram for describing transmission paths of power and a signal in the artificial leg according to the embodiment.

Next, with reference to FIGS. 2 and 3, an artificial leg 1 according to an embodiment of the present disclosure will be described. FIG. 2 is a schematic diagram illustrating an example of the schematic configuration of the artificial leg 1 according to the present embodiment. FIG. 3 is an explanatory diagram for describing transmission paths of power and a signal in the artificial leg 1 according to the present embodiment. Note that FIG. 3 uses a solid line arrow and a dashed line arrow to illustrate transmission paths of power and a signal, respectively.

The artificial leg 1 according to the present embodiment is worn and used by a wearer user, and used to support the weight of the user. As illustrated in FIG. 1, the artificial leg 1 includes a thigh side member 100, a lower leg side member 200, and an actuator 320 that connects the thigh side member 100 to the lower leg side member 200.

The thigh side member 100 includes a connection section 110 that is connected to a socket member which is not illustrated, but accommodates an attachment target portion of a user for the artificial leg 1, and a main body section 120 that is connected to the actuator 320. In the state in which the artificial leg 1 is used by a user, the connection section 110 is positioned on the upper side of the thigh side member 100 in the perpendicular direction, and the socket member opens upward in the perpendicular direction. The main body section 120 has a substantially cylindrical shape. The main body section 120 has an internal space.

The internal space can accommodate a variety of members. For example, the internal space of the main body section 120 may accommodate the actuator 320 and the upper end of an extending section 210 of the lower leg side member 200. In that case, the main body section 120 is connected to the upper end side of the extending section 210 via the actuator 320 on the internal side. Note that the internal space of the main body section 120 may accommodate a drive motor 340 and a gear box 330.

The lower leg side member 200 includes the extending section 210 that is connected to the actuator 320, and a ground contact section 220 that abuts on the floor in the state in which the artificial leg 1 is used by a user. The extending section 210 is connected to the main body section 120 of the thigh side member 100 via the actuator 320 on the upper end side, and is relatively pivotable with respect to the thigh side member 100. In addition, the pivotal direction of the extending section 210 is guided, for example, by the main body section 120 of the thigh side member 100. Specifically, the extending section 210 can be configured to be pivotable on the central axis of the main body section 120. The upper part of the ground contact section 220 is connected to the lower end side of the extending section 210, and the lower part of the ground contact section 220 abuts on the floor. Specifically, the ground contact section 220 is shaped to be bent substantially at the right angle. The part of the ground contact section 220 extending in the perpendicular direction is connected to the lower end side of the extending section 210, and the part of the ground contact section 220 extending in the horizontal direction abuts on the floor.

The actuator 320 transmits torque to the lower leg side member 200 to relatively pivot the lower leg side member 200 with respect to the thigh side member 100. The actuator 320 is connected to the drive motor 340 via the gear box 330. As illustrated in FIG. 3, the actuator 320 is configured such that the toque output from the drive motor 340 is input into the actuator 320 via the gear box 330. The gear box 330 is connected to an output shaft 342 of the drive motor 340. In addition, the actuator 320 is connected to an output shaft 332 of the gear box 330. The gear box 330 converts the torque output from the drive motor 340 at a predetermined deceleration ratio, and outputs the converted torque to the actuator 320.

The actuator 320 is provided with a leaf spring. The torque output from the drive motor 340 is transmitted to the lower leg side member 200 serving as a target object on the output side via the leaf spring. In addition, the artificial leg 1 is provided with a displacement sensor 350 that detects the displacement amount of the leaf spring of the actuator 320. A detection result acquired by the displacement sensor 350 is output to a control apparatus 400, and used for processing by the control apparatus 400. The control apparatus 400 outputs an operation instruction to control the driving of the drive motor 340.

Specifically, the control apparatus 400 controls the driving of the drive motor 340 on the basis of the detection result acquired by the displacement sensor 350. More specifically, the control apparatus 400 calculates a load applied to the leaf spring on the basis of a measurement value of the displacement amount of the leaf spring corresponding to the detection result. Then, the control apparatus 400 calculates the torque actually transmitted to the lower leg side member 200 via the leaf spring on the basis of the calculated value of the load. Then, the control apparatus 400 controls the driving of the drive motor 340 on the basis of the calculated value of the torque such that the torque transmitted to the lower leg side member 200 approximates a target value.

According to the present embodiment, in the case where torque transmitted by the leaf spring is greater than a predetermined value in the actuator 320, providing a support member that supports a part of the leaf spring on the deflection direction side makes it possible to miniaturize the apparatus. The details of the actuator 320 like this will be described below.

3. OVERVIEW OF THE PRESENT TECHNOLOGY

Next, with reference to FIGS. 4 to 14, the overview of the present technology will be described before the details of the actuator 320 according to an embodiment of the present disclosure are described. Specifically what helps easily understand the deformation and a mechanical characteristic of the leaf spring of the actuator 320 described below will be described.

[3-1. Deformation of Leaf Spring]

First, with reference to FIGS. 4 to 11, the deformation of a leaf spring 910 will be described. The following describes the deformation of the leaf spring 910 at the time when a load P is applied to an opposite end 910b of the leaf spring 910 in the plate thickness direction in a system including the leaf spring 910 whose one end 910a is cantilevered, and a deformation guide 920 that can support a part of the leaf spring on the deflection direction side. The leaf spring 910 is capable of deflection deformation in the plate thickness direction in accordance with the load P. In addition, the deformation guide 920 is provided close to the part of the one end 910a side of the leaf spring 910 in the plate thickness direction of the leaf spring 910. In the case where the load P is greater than the predetermined value, the deformation guide 920 supports the part of the one end 910a side of the leaf spring 910 on the deflection direction side.

Figure 4:
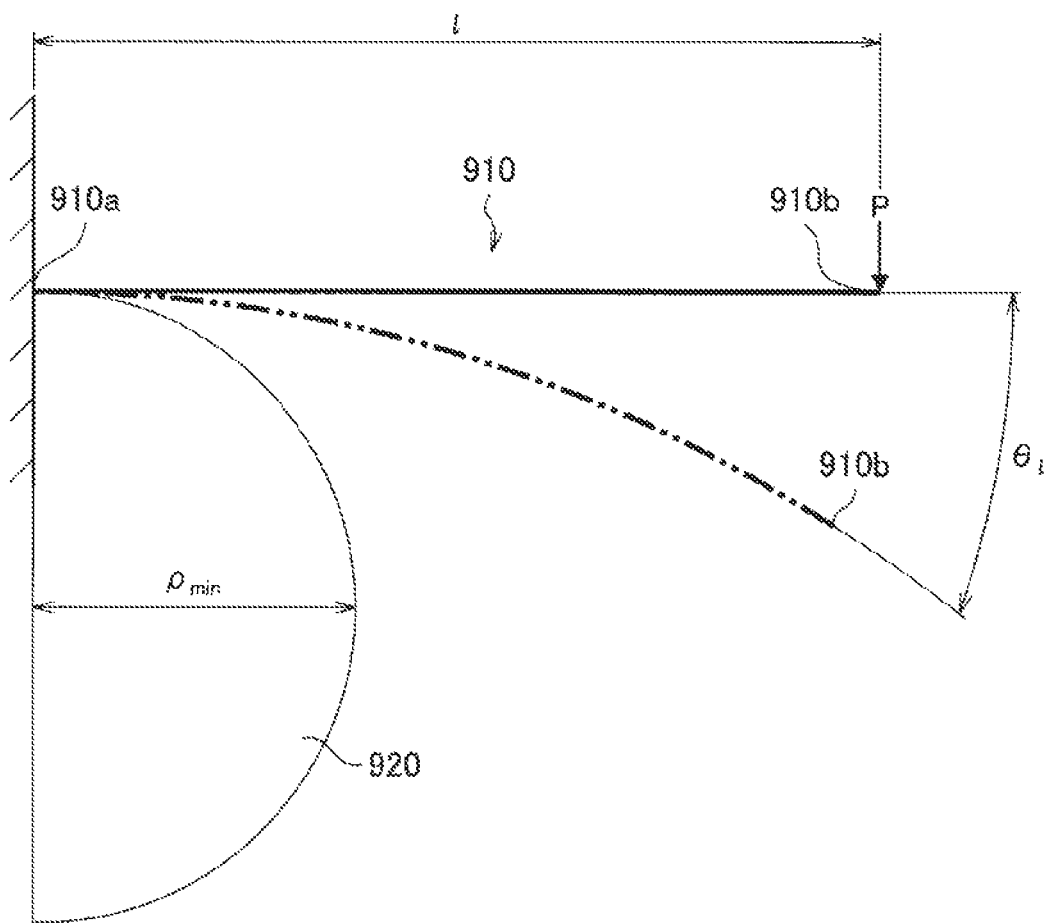
FIG. 4 is an explanatory diagram illustrating that a leaf spring is deformed in a state in which a part of one end side of the leaf spring does not abut on a deformation guide.
Figure 8:
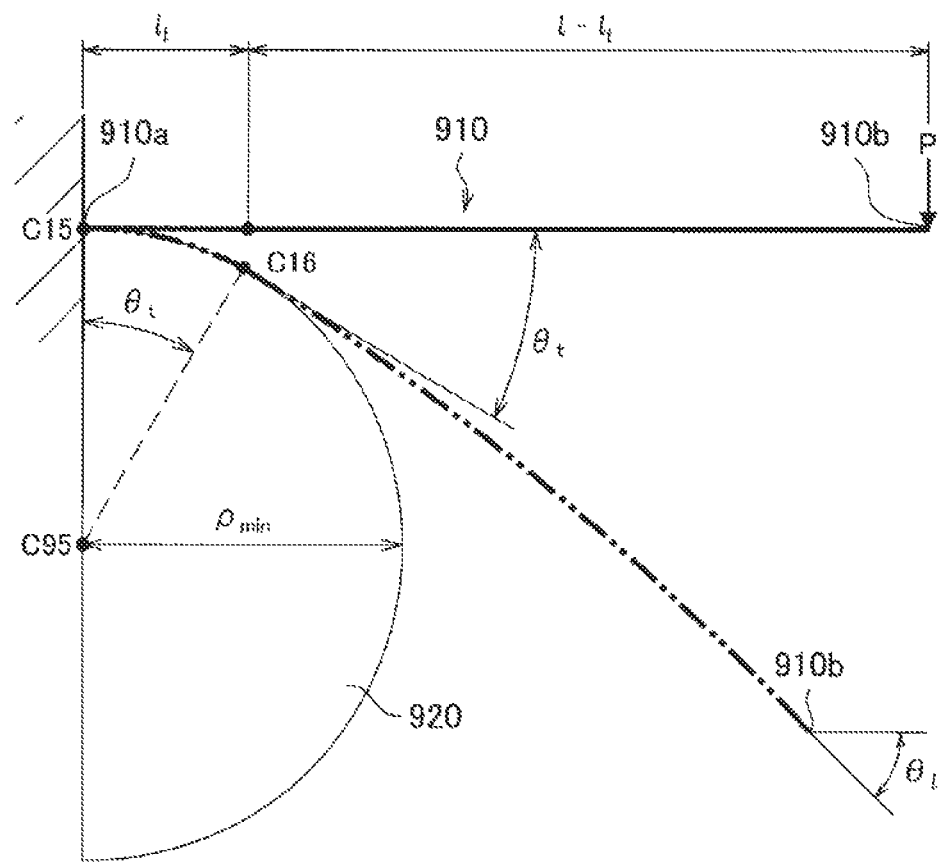
FIG. 8 is an explanatory diagram illustrating that a leaf spring is deformed in a state in which a part of one end side of the leaf spring abuts on a deformation guide.

FIGS. 4 and 8 schematically illustrate the leaf spring 910 and the deformation guide 920 like these with cross-sectional views for cross sections orthogonal to the width direction of the leaf spring 910. In addition, FIGS. 4 and 8 schematically illustrate neutral axes of the leaf spring 910 as the shape of the leaf spring 910. Specifically, a deflection curve showing a neutral axis of the leaf spring 910 in the case where deflection deformation occurs is illustrated as a two-dot chain line, and a neutral axis of the leaf spring 910 in the case where no deflection deformation occurs is illustrated as a solid line. Note that the cross-sectional shape of the leaf spring 910 is rectangular. In addition, the plate thickness of the leaf spring 910 is represented as d, a second area moment is represented as I, Young's modulus is represented as E, and length in the longitudinal direction is represented as 1.

(Deformation Guide)

First, the deformation guide 920 will be described. The deformation guide 920 is provided to prevent the leaf spring 910 from being broken by the applied load P. Specifically, the deformation guide 920 is provided to prevent plastic deformation from being caused by the load P in the leaf spring 910. The relationship between a bending moment M imparted to the leaf spring 910 and a curvature radius p of a neutral axis of the leaf spring 910 is expressed with the following formula (1).

[Math. 1]

$$\frac{1}{\rho} = \frac{M}{EI} \quad (1)$$

In addition, distortion occurring in the leaf spring 910 in the longitudinal direction is the greatest at an end in the plate thickness direction. Distortion a at an end in the plate thickness direction is expressed with the following formula (2).

[Math. 2]

$$\varepsilon = \frac{d}{2\rho} = d\frac{M}{2EI} \quad (2)$$

The dimension of the deformation guide 920 can be set such that, for example, in the case where an upper limit value of distortion in an elasticity region of a material included in the leaf spring 910 is εmax, distortion greater than the predetermined allowable distortion corresponding to the upper limit value εmax does not occur in the leaf spring 910. As allowable distortion, for example, a value obtained by dividing the upper limit value εmax of distortion by a safety factor n (≥1) can be set. When the allowable distortion occurs in the leaf spring 910, the bending moment imparted to the leaf spring 910 has an upper limit value Mmax and the curvature radius of the leaf spring 910 has a lower limit value ρmin. Therefore, the following formula (3) showing the relationship between the upper limit value εmax of distortion and the upper limit value Mmax of a bending moment is derived from the formula (2).

[Math. 3]

$$\frac{\varepsilon_{max}}{n} = d\frac{M_{max}}{2EI} \quad (3)$$

In addition, the following formula (4) is derived by transforming the formula (3).

[Math. 4]

$$M_{max} = \frac{2EI}{d}\frac{\varepsilon_{max}}{n} \quad (4)$$

In addition, the following formula (5) showing the relationship between the lower limit value ρmin of a curvature radius and the upper limit value Mmax of a bending moment is derived from the formula (1).

[Math. 5]

$$\rho_{min} = \frac{EI}{M_{max}} \quad (5)$$

In addition, the following formula (6) showing the relationship between the upper limit value max of distortion and the lower limit value ρmin of a curvature radius is derived by substituting the formula (4) into the formula (5).

[Math. 6]

$$\rho_{min} = n\frac{d}{2\varepsilon_{max}} \quad (6)$$

The deformation guide 920 has a cross-sectional shape like a semicircle, for example, as illustrated in FIGS. 4 and 8, and extends in the width direction of the leaf spring 910. Specifically, as the radius of the deformation guide 920, the lower limit value ρmin of the curvature radius calculated on the basis of the formula (6) can be set. Here, the bending moment imparted to the leaf spring 910 by the load P is the greatest as described below at the one end 910a to be cantilevered among the respective positions in the leaf spring 910. Therefore, the curvature radius of the leaf spring 910 is the smallest at the one end 910a among the respective positions in the leaf spring 910.

In the case where the load P is small to the degree to which the bending moment imparted to the one end 910a of the leaf spring 910 is less than or equal to the upper limit value Mmax, the curvature radius at the one end 910a is greater than or equal to the lower limit value ρmin. Therefore, in such a case, as illustrated in FIG. 4, the part of the one end 910a side of the leaf spring 910 does not abut on the outer peripheral part of the deformation guide 920. Here, the process in which the load P increases from a relatively small value will be considered. When the bending moment imparted to the one end 910a of the leaf spring 910 reaches the upper limit value Mmax, the curvature radius at the one end 910a reaches the lower limit value ρmin. In the case where the load P further increases, the part of the one end 910a side of the leaf spring 910 abuts on the outer peripheral part of the deformation guide 920 in the state in which the curvature radius is maintained at the lower limit value ρmin. That causes the part of the one end 910a side of the leaf spring 910 to be supported by the deformation guide 920 on the deflection direction side. Therefore, it is possible to prevent the deformation of the leaf spring 910 which causes the curvature radius to be smaller than the lower limit value ρmin. Accordingly, it is possible to prevent plastic deformation from occurring in the leaf spring 910.

In this way, in the case where the load P is smaller than or equal to the predetermined value, the part of the one end 910a side of the leaf spring 910 does not abut on the outer peripheral part of the deformation guide 920. In contrast, in the case where the load P is greater than the predetermined value, the part of the one end 910a side of the leaf spring 910 abuts on the outer peripheral part of the deformation guide 920, and is supported by the deformation guide 920 on the deflection direction side. The predetermined value can correspond to the value of the load P at the time when the bending moment imparted to the one end 910a of the leaf spring 910 reaches the upper limit value Mmax, for example, in the process in which the load P is increased from a relatively small value.

(Deformation of Leaf Spring in Case where Applied Load is Smaller than or Equal to Predetermined Value)

Next, with reference to FIGS. 4 to 7, the deformation of the leaf spring 910 in the case where the applied load P is smaller than or equal to the predetermined value will be described. In the case where the load P is smaller than or equal to the predetermined value, the part of the one end 910a side of the leaf spring 910 does not abut on the deformation guide 920. FIG. 4 illustrates that the leaf spring 910 is deformed in the state in which the part of the one end 910a side of the leaf spring 910 does not abut on the deformation guide 920.

Figure 5:
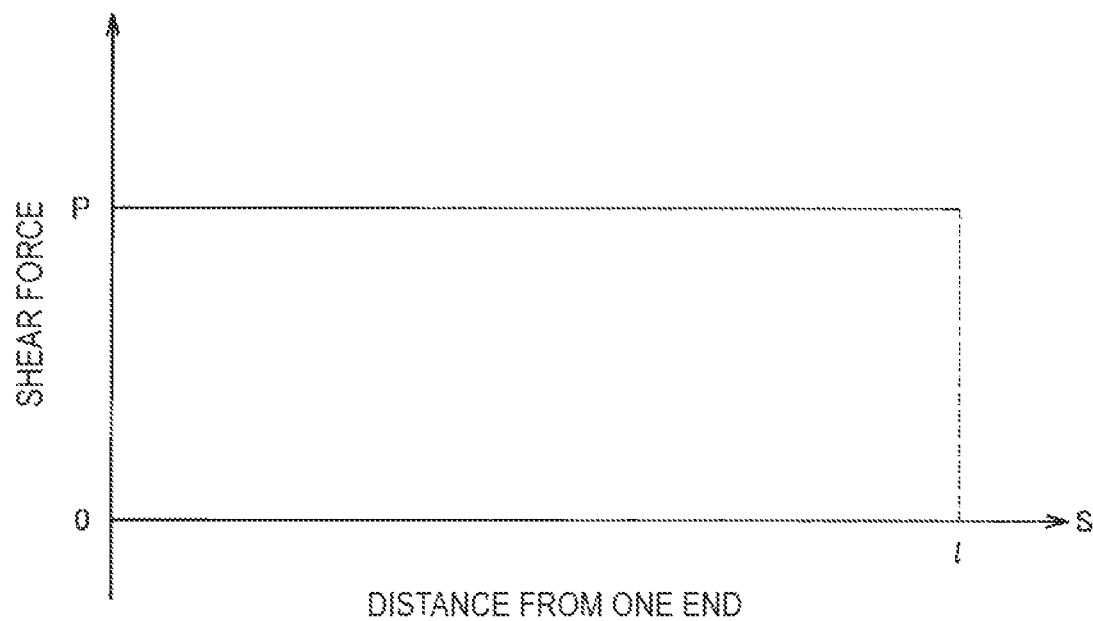
FIG. 5 is a shear force diagram for the leaf spring in the state illustrated in FIG. 4.

FIG. 5 is a shear force diagram referred to as sheer force diagram (SFD) for the leaf spring 910 in the state illustrated in FIG. 4. In the SFD in FIG. 5, the relationship is shown between a distance s from the one end 910a in the longitudinal direction and applied shear force in the leaf spring 910. As illustrated in FIG. 5, in the case where the applied load P is smaller than or equal to the predetermined value, the shear force imparted to the leaf spring 910 has the same value at the position corresponding to each distance s. Specifically, the shear force imparted to the leaf spring 910 has the value equal to the load P at the position corresponding to each distance s.

Figure 6:
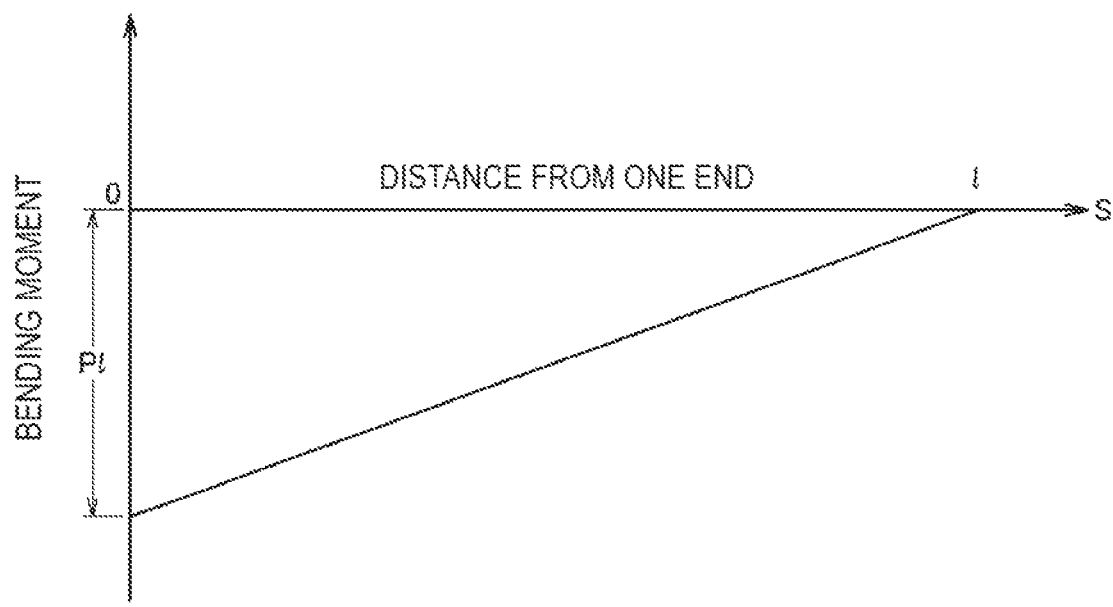
FIG. 6 is a bending moment diagram for the leaf spring in the state illustrated in FIG. 4.

FIG. 6 is a bending moment diagram referred to as bending moment diagram (BMD) for the leaf spring 910 in the state illustrated in FIG. 4. In the BMD in FIG. 6, the relationship is shown between a distance s from the one end 910a in the longitudinal direction and an applied bending moment in the leaf spring 910. Note that the change ratio of a bending moment with respect to the longitudinal direction agrees with shear force in the leaf spring 910. Therefore, the bending moment shown by the BMD in FIG. 6 and the shear force shown by the SFD in FIG. 5 have such a relationship. As illustrated in FIG. 6, in the case where the applied load P is smaller than or equal to the predetermined value, the absolute value of the bending moment imparted to the leaf spring 910 increases from the opposite end 910b side to the one end 910a side. Note that the BMDs in FIGS. 6 and 11 express the value of a bending moment by taking the positive/negative direction into consideration. However, the following description expresses the value of a bending moment as an absolute value without taking the positive/negative direction into consideration.

Here, the bending moment M of the leaf spring 910 in each distance s is expressed with the following formula (7) on the basis of the balance of a moment in the virtual cross section corresponding to each distance s.

[Math. 7]

$$M = P(l-s) \quad (7)$$

According to the formula (7), the absolute value of the bending moment imparted to the leaf spring 910 is 0 at the opposite end 910b6, and is Pl at the one end 910a as shown in the BMD in FIG. 6. In this way, the bending moment imparted to the leaf spring 910 is the greatest at the one end 910a to be cantilevered among the respective positions in the leaf spring 910. The following also refers to such a bending moment at the one end 910a as maxM(s).

In addition, the curvature radius of the leaf spring 910 is the smallest at the one end 910a among the respective positions in the leaf spring 910. The following also refers to such a curvature radius at the one end 910a as min ρ(s). In the case where the load P is smaller than or equal to the predetermined value, as described above, the curvature radius min ρ(s) at the one end 910a is greater than or equal to the lower limit value ρmin. Accordingly, the following formula (8) holds.

[Math. 8]

$$\rho_{min} \leq \min \rho(s) \quad (8)$$

In addition, in the case where the load P is smaller than or equal to the predetermined value, as described above, the bending moment MaxM(s) at the one end 910a is smaller than or equal to the upper limit value Mmax. Moreover, according to the formula (7), the bending moment MaxM(s) at the one end 910a is Pl. Therefore, the following formula (9) holds.

[Math. 9]

$$M_{max} \geq \max M(s) = Pl \quad (9)$$

Here, the following formula (10) is derived by transforming the formula (5).

[Math. 10]

$$M_{max} = \frac{EI}{\rho_{min}} \quad (10)$$

The following formula (11) is derived by substituting the formula (10) into the formula (9) and arranging the resultant formula.

[Math. 11]

$$\frac{EI}{l \cdot \rho_{min}} \geq P \quad (11)$$

According to the formula (11), in the case where the load P is smaller than or equal to EI/l·ρmin, the curvature radius min ρ(s) at the one end 910a is greater than or equal to the lower limit value ρmin. Accordingly, the part of the one end 910a side of the leaf spring 910 does not abut on the deformation guide 920. Therefore, in the case where the load P is smaller than or equal to EI/l·ρmin, the leaf spring 910 is in the state illustrated in FIG. 4.

Figure 7:
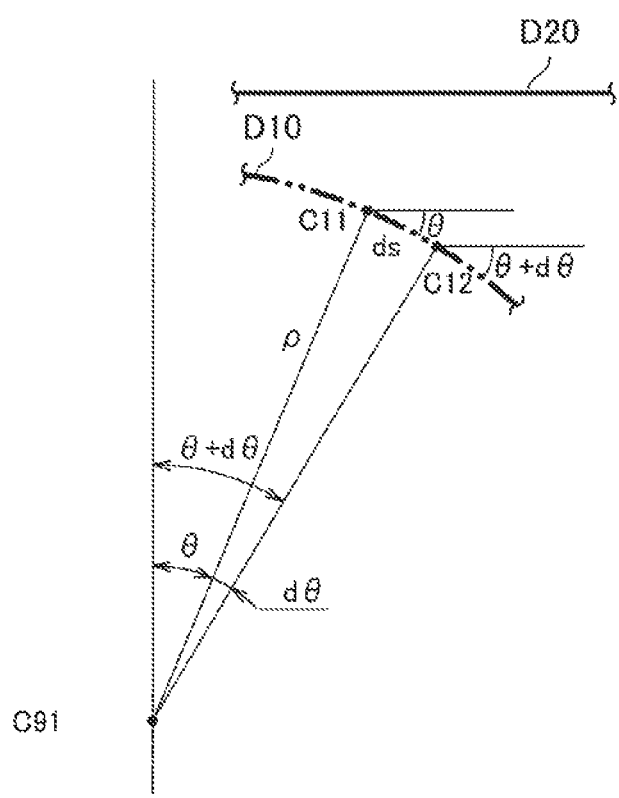
FIG. 7 is an explanatory diagram for describing a relationship between a deflection angle θ and a distance s.

Here, the relationship between a deflection angle θ in the leaf spring 910 and the distance s from the one end 910a in the longitudinal direction will be described. FIG. 7 is an explanatory diagram for describing the relationship between the deflection angle θ and the distance s. FIG. 7 schematically illustrates a deflection curve D10 showing a neutral axis of the leaf spring 910 in the case where deflection deformation occurs, and a straight line D20 showing a neutral axis of the leaf spring 910 in the case where no deflection deformation occurs. As illustrated in FIG. 7, the deflection angles for a point C11 and a point C12 positioned on the deflection curve D10 with an infinitesimal distance ds in between are set as θ and θ+dθ, respectively. Note that the deflection angle at each point on the deflection curve D10 is an angle formed between the tangent line of the deflection curve D10 at the point and the straight line D20. In addition, the curvature radius of the arc between the point C11 and the point C12 is set as ρ, and the curvature center is set as a point C91.

In this case, as illustrated in FIG. 7, the angle formed between the straight line connecting the point C91 to the point C11 and the straight line orthogonal to the straight line D20 is θ. In addition, the angle formed between the straight line connecting to a point C90 to the point C12 and the straight line orthogonal to the straight line D20 is θ+dθ. Therefore, the angle formed between the straight line connecting the point C91 to the point C11 and the straight line connecting the point C91 to the point C12 is dθ. Here, dθ is an infinitesimal angle. Accordingly, an infinitesimal distance ds corresponding to the length of an arc between the point C11 and the point C12 is obtained by multiplying the curvature radius ρ by dθ that is the angle formed between the straight line connecting the point C91 to the point C11 and the straight line connecting the point C91 to the point C12. Therefore, the following formula (12) holds.

[Math. 12]

$$\rho d\theta = ds \qquad (12)$$

In addition, the formula (1) and the formula (12) are simultaneously solved, and ρ is deleted to derive the following formula (13).

[Math. 13]

$$\frac{d\theta}{ds} = \frac{M}{EI} \qquad (13)$$

Here, an opposite end deflection angle θ1 that is the deflection angle at the opposite end 910b corresponds to a value obtained by integrating the deflection angle θ with respect to the distance s from 0 to 1, so that the following formula (14) holds.

[Math. 14]

$$\theta_l = \int_{S=0}^{S=l} d\theta = \int_0^l \frac{d\theta}{ds} ds \qquad (14)$$

Here, the formula (13) is substituted into the formula (14) to derive the following formula (15).

[Math. 15]

$$\theta_l = \frac{1}{EI} \int_0^l M ds \qquad (15)$$

Here, the formula (7) is substituted into the formula (15) and arranged to derive the following formula (16).

[Math. 16]

$$\theta_l = \frac{1}{EI} \int_0^l P(l-s) ds = \frac{P}{EI} \frac{l^2}{2} \qquad (16)$$

As described above, in the case where the load P is smaller than or equal to EI/l·ρmin, the part of the one end 910a side of the leaf spring 910 does not abut on the deformation guide 920. In such a case, the opposite end deflection angle θ1 that is the deflection angle at the opposite end 910b is expressed with the formula (16).

(Deformation of Leaf Spring in Case where Applied Load is Greater than Predetermined Value)

Next, with reference to FIGS. 8 to 11, the deformation of the leaf spring 910 in the case where the applied load P is greater than the predetermined value will be described. In the case where the load P is greater than the predetermined value, the part of the one end 910a side of the leaf spring 910 abuts on the deformation guide 920. FIG. 8 illustrates that the leaf spring 910 is deformed in the state in which the part of the one end 910a side of the leaf spring 910 abuts on the deformation guide 920.

Figure 9:
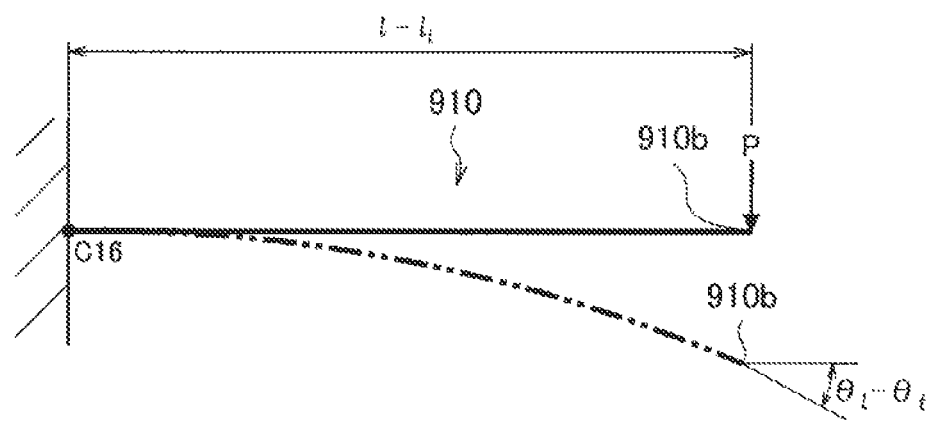
FIG. 9 is an explanatory diagram for describing that an opposite end side of the leaf spring is deformed in the state in which the part of the one end side of the leaf spring abuts on the deformation guide.

As illustrated in FIG. 8, on the one end 910a side of the leaf spring 910, the part whose distance s from the one end 910a in the longitudinal direction ranges from 0 to lt is taken to be a part that abuts on the deformation guide 920. In addition, as illustrated in FIG. 8, on the deflection curve illustrated as a two-dot chain line, a point positioned to separate from the one end 910a with the distance lt in the longitudinal direction is set as a point C16. Specifically, the point C16 corresponds to a point on a neutral axis of the leaf spring 910 with respect to the end of the part of the leaf spring 910 abutting on the deformation guide 920 which is opposite to the one end 910a. In this case, as illustrated in FIG. 9, the part of the leaf spring 910 closer to the opposite end 910b side than the point C16 can correspond to a virtual leaf spring in which the point C16 is cantilevered.

Figure 10:
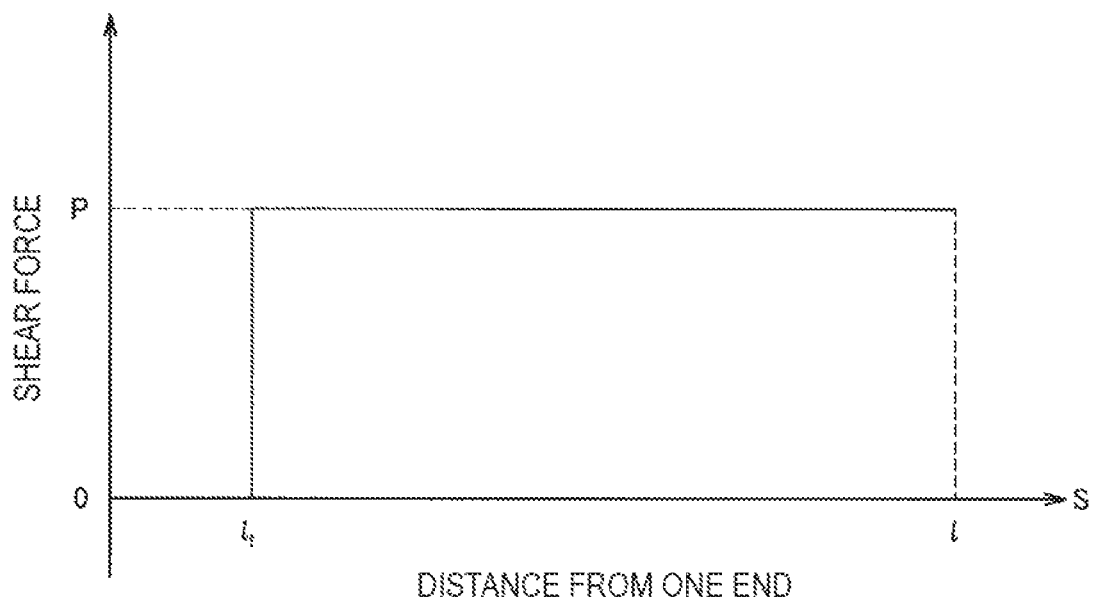
FIG. 10 is a shear force diagram for the leaf spring in the state illustrated in FIG. 8.

FIG. 10 is an SFD for the leaf spring 910 in the state illustrated in FIG. 8. As illustrated in FIG. 10, in the case where the applied load P is greater than the predetermined value, the shear force imparted to the leaf spring 910 is 0 in the part of the one end 910a side. The part of the one end 910a side of the leaf spring 910 with a distance s of 0 to lt is supported by the deformation guide 920. Accordingly, the shear force of the part is 0. Therefore, specifically the shear force imparted to the leaf spring 910 is 0 in the part having a distance s of 0 to lt, and has a value equal to the load P in the part having a distance s of lt to 1.

Figure 11:
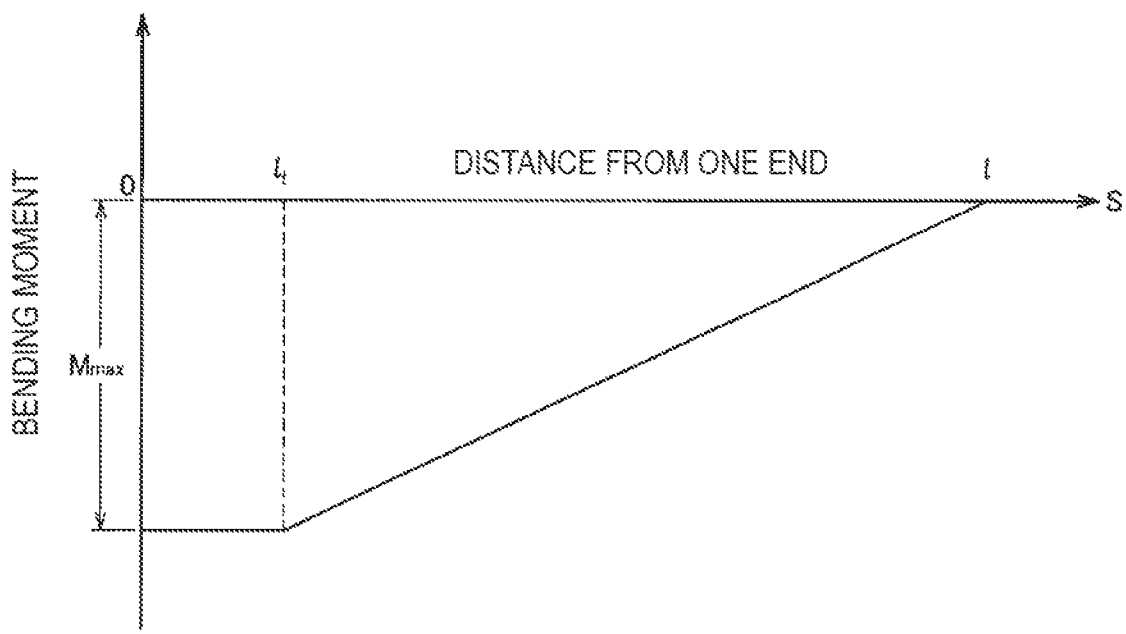
FIG. 11 is a bending moment diagram for the leaf spring in the state illustrated in FIG. 8.

FIG. 11 is a BMD for the leaf spring 910 in the state illustrated in FIG. 8. Note that, as described above, the change ratio of a bending moment with respect to the longitudinal direction agrees with shear force in the leaf spring 910. Therefore, the bending moment shown by the BMD in FIG. 11 and the shear force shown by the SFD in FIG. 10 have such a relationship. As illustrated in FIG. 11, the absolute value of the bending moment imparted to the leaf spring 910 is the upper limit value Mmax in the part of the one end 910a. Specifically, on the one end 910a side of the leaf spring 910, the curvature radius of the part having a distance s of 0 to lt is the lower limit value ρmin. Accordingly, in the part, the absolute value of the bending moment is the upper limit value Mmax. Therefore, the absolute value of the bending moment imparted to the leaf spring 910 increases from the opposite end 910b side to the one end 910*a* side in the part having a distance s of lt to 1, and is the upper limit value Mmax in the part having a distance s from 0 to lt.

Here, the upper limit value Mmax is expressed with the following formula (17) on the basis of the balance of a moment with respect to the position having a distance s of lt in a virtual cross section.

[Math. 17]

$$M_{max} = \int_{l_t}^{l} P\, ds = P(l - l_t) \tag{17}$$

In addition, the following formula (18) is derived by transforming the formula (17).

[Math. 18]

$$l - l_t = \frac{M_{max}}{P} \tag{18}$$

Here, as illustrated in FIG. 8, the central point of a semicircle showing a cross section of the deformation guide 920 is set as a point C95. A point on a neutral axis of the leaf spring 910 with respect to the one end 910*a* is set a point C15. The angle formed between the straight line connecting the point C95 to the point C15 and the straight line connecting the point C95 to the point C16 is set as θt. Here, θt is an infinitesimal angle. Accordingly, lt corresponding to the length of an arc between the point C15 and the point C16 is obtained by multiplying θt by the lower limit value ρmin. θt is the angle formed between the straight line connecting the point C95 to the point C15 and the straight line connecting the point C95 to the point C16. The lower limit value ρmin is the radius of the deformation guide 920. Therefore, the following formula (19) holds.

[Math. 19]

$$\theta_t = \frac{l_t}{\rho_{min}} \tag{19}$$

Here, the deflection angle of the leaf spring 910 at the point C16 is θt as illustrated in FIG. 8. Therefore, the virtual leaf spring in which the point C16 illustrated in FIG. 9 is cantilevered extends in the direction inclined by θt in the deflection direction with respect to the longitudinal direction of the leaf spring 910 in the case where no deflection deformation occurs as the virtual leaf spring. Therefore, as illustrated in FIG. 9, the deflection angle at the opposite end 910*b* of the virtual leaf spring corresponds to the value obtained by subtracting θt from the opposite end deflection angle θ1 of the leaf spring 910 illustrated in FIG. 8.

Here, the deflection angle (θ1−θt) at the opposite end 910*b* of the virtual leaf spring can be expressed with a formula obtained by converting the integration section with respect to the distance s on the right side of the formula (15) into a section from lt to 1. Accordingly, the following formula (20) holds.

[Math. 20]

$$\theta_l - \theta_t = \frac{1}{EI}\int_{l_t}^{l} M\, ds \tag{20}$$

In addition, the formula (7) is substituted into the formula (20) and arranged to derive the following formula (21).

[Math. 21]

$$\theta_l - \theta_t = \frac{1}{EI}\int_{l_t}^{l} P(l-s)\, ds = \frac{P}{EI}\frac{(l-l_t)^2}{2} \tag{21}$$

In addition, the formula (7) is substituted into the formula (21) to derive the following formula (22).

[Math. 22]

$$\theta_l - \theta_t = \frac{1}{EI} M_{max} \frac{l - l_t}{2} \tag{22}$$

In addition, the formula (5) and the formula (22) are simultaneously solved, and the upper limit value Mmax is deleted to derive the following formula (23).

[Math. 23]

$$\theta_l - \theta_t = \frac{1}{\rho_{min}} \frac{l - l_t}{2} \tag{23}$$

In addition, the formula (19) is substituted into the formula (23) and arranged to derive the following formula (24).

[Math. 24]

$$\theta_l = \frac{1}{\rho_{min}} \frac{l + l_t}{2} \tag{24}$$

In addition, the formula (18) and the formula (24) are simultaneously solved, and lt is deleted to derive the following formula (25).

[Math. 25]

$$\theta_l = \frac{1}{\rho_{min}} \frac{2l - M_{max}/P}{2} \tag{25}$$

In addition, the formula (5) and the formula (25) are simultaneously solved, and the upper limit value Mmax is deleted to derive the following formula (26).

[Math. 26]

$$\theta_l = \frac{1}{\rho_{min}} - \frac{1}{2\rho_{min}^2}\frac{EI}{P} \tag{26}$$

As described above, in the case where the load P is greater than EI/l·ρmin, the part of the one end 910*a* side of the leaf spring 910 abuts on the deformation guide 920. In such a case, the opposite end deflection angle θ1 that is the deflection angle at the opposite end 910*b* is expressed with the formula (26).

[3-2. Mechanical Characteristic of Leaf Spring]

Next, with reference to FIGS. 12 to 15, a mechanical characteristic of the leaf spring 910 will be described. The following describes, as an example, the case where length l in the longitudinal direction is set as 30 [mm], plate thickness d is set as 0.6 [mm], width w is set as 3 [mm], Young's modulus E is set as 200 [GPa], the upper limit value εmax of distortion is set as 2.5×10.3, and the safety factor n is set as 1.5 for the specifications of the leaf spring 910.

In the case where the specifications of the leaf spring 910 are set as described above, the second area moment I of the leaf spring 910 is expressed with the following formula (27).

[Math. 27]

$$I = \frac{wd^3}{12} = 0.05 [\text{mm}^4] \tag{27}$$

In addition, the lower limit value ρmin of a curvature radius is expressed with the following formula (28).

[Math. 28]

$$\rho_{min} = n \frac{d}{2\varepsilon_{max}} = 180 [\text{mm}] \tag{28}$$

Therefore, the radius of the deformation guide 920 is set at 180 [mm], which is the lower limit value ρmin shown in the formula (28).

In the process in which the load P increases from a relatively small value, the predetermined value corresponding to the load P at the time when the state in which a part of the leaf spring 910 does not abut on the deformation guide 920 is switched to the state in which a part of the leaf spring 910 abuts on the deformation guide 920 is EI/l·ρmin. In the case where the specifications of the leaf spring 910 are set as described above, the predetermined value is 1.85 [N].

Figure 12:
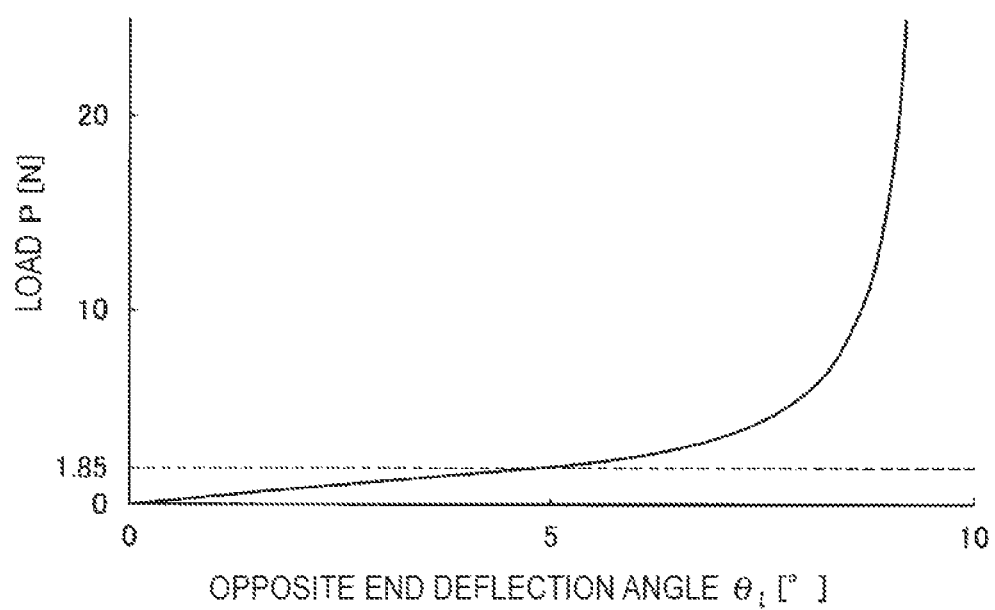
FIG. 12 is an explanatory diagram illustrating an example of a relationship between an opposite end deflection angle θ1 of the leaf spring and a load P applied to the leaf spring.

FIG. 12 is an explanatory diagram illustrating an example of the relationship between the opposite end deflection angle θ1 of the leaf spring 910 and the load P applied to the leaf spring 910. FIG. 12 illustrates the relationship between the opposite end deflection angle θ1 and the load P which is defined by the formula (16) and the formula (26). Specifically, the use of the formula (16) makes it possible to calculate, for each of the loads P smaller than or equal to 1.85 [N], the corresponding opposite end deflection angle θ1. In addition, the use of the formula (26) makes it possible to calculate, for each of the loads P greater than 1.85 [N], the corresponding opposite end deflection angle 81. A result obtained according to such calculation is illustrated in FIG. 12.

Figure 13:
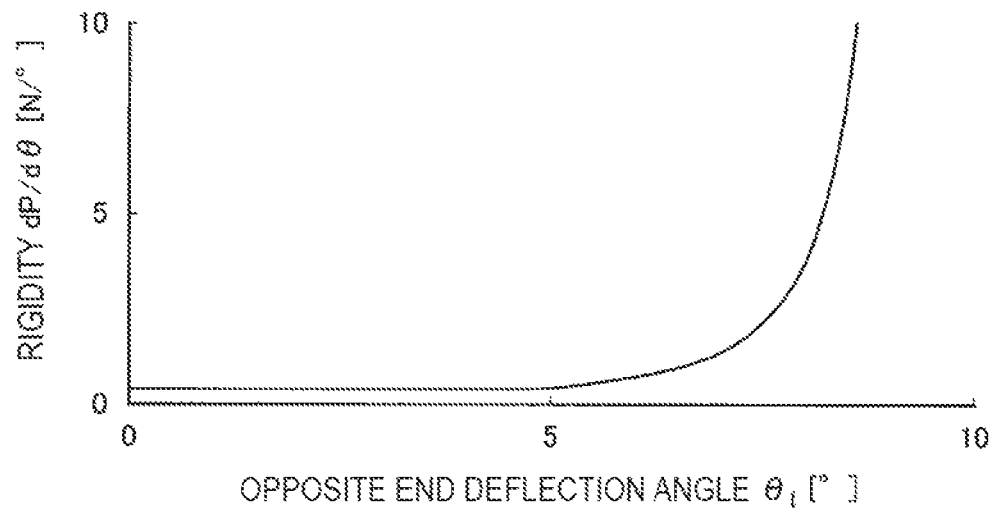
FIG. 13 is an explanatory diagram illustrating an example of the relationship between the opposite end deflection angle θ1 and the rigidity of the leaf spring 910.

FIG. 13 is an explanatory diagram illustrating an example of the relationship between the opposite end deflection angle θ1 and the rigidity of the leaf spring 910. The rigidity of the leaf spring 910 indicates the degree of difficulty in deformation of the leaf spring 910 against the load P, and can be calculated on the basis of the relationship between the opposite end deflection angle θ1 and the load P illustrated in FIG. 12. Specifically, the rigidity with respect to each opposite end deflection angle θ1 can be calculated by differentiating the load P with respect to the opposite end deflection angle θ1 on the basis of the relationship between the opposite end deflection angle θ1 and the load P illustrated in FIG. 12. A result obtained according to such calculation is illustrated in FIG. 13.

If the deformation guide 920 is not provided to the leaf spring 910, the load P exceeding 1.85 [N] allows the leaf spring 910 to deform such that the curvature radius at the one end 910a is smaller than the lower limit value ρmin. That can cause plastic deformation in the leaf spring 910.

Meanwhile, in the system illustrated in FIGS. 4 and 8, providing the deformation guide 920 to the leaf spring 910 causes the part of the one end 910a side of the leaf spring 910 to be supported by the deformation guide 920 on the deflection direction side in the case where the load P exceeds 1.85 [N]. Even in the case where the load P exceeds 1.85 [N], that can prevent such deformation of the leaf spring 910 that the curvature radius is smaller than the lower limit value ρmin.

In this way, in the case where the load P is relatively large, it is possible to secure the state in which the rigidity of the leaf spring 910 is high. FIG. 13 illustrates that, in the case where the opposite end deflection angle θ1 having a correlation with the load P is relatively large, the rigidity of the leaf spring 910 is relatively high. Specifically, the rigidity of the leaf spring 910 increase with increase in the load P and the opposite end deflection angle θ1 in the case where the load P and the opposite end deflection angle θ1 are relatively large. Therefore, the leaf spring 910 is capable of elastic deformation in the displacement amount corresponding to each load P even in the case where the load P exceeds 1.85 [N] as illustrated in FIG. 12. Accordingly, it is possible to prevent plastic deformation from occurring in the leaf spring 910.

Here, a load change ratio regarding the leaf spring 910 will be described. The load change ratio indicates the degree of change in the load P in the case where the opposite end deflection angle θ1 fluctuates. Specifically, the load change ratio is a change ratio of the load P before and after a fluctuation of 0.1° in the opposite end deflection angle θ1. Therefore, the load change ratio has relevancy to measurement accuracy in the case where a measurement value of the opposite end deflection angle θ1 as the displacement amount of the leaf spring 910 is used to measure the load P applied to the leaf spring 910. Specifically, as the load change ratio is lower, the measurement accuracy is higher. Meanwhile, as the load change ratio is higher, the measurement accuracy is lower.

Figure 14:
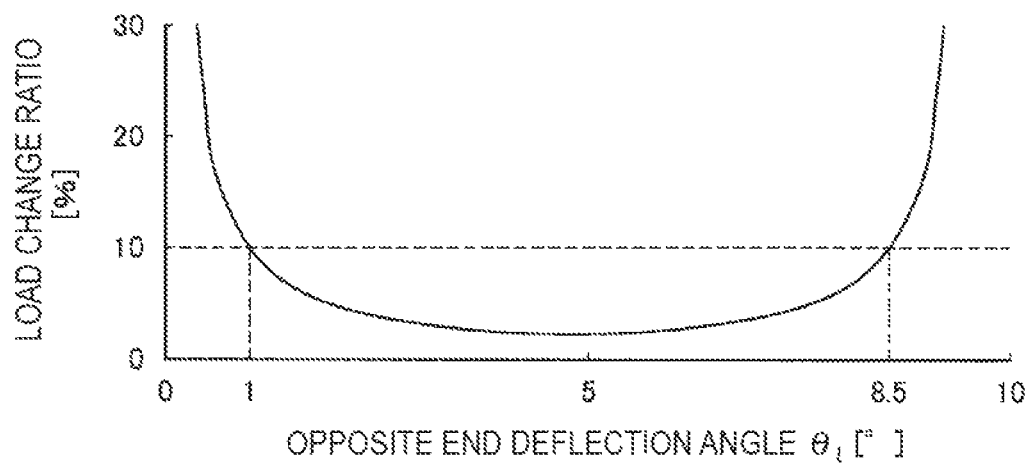
FIG. 14 is an explanatory diagram illustrating an example of a relationship between the opposite end deflection angle θ1 of the leaf spring and a load change ratio.

FIG. 14 is an explanatory diagram illustrating an example of the relationship between the opposite end deflection angle θ1 of the leaf spring 910 and a load change ratio. The load change ratio regarding each opposite end deflection angle θ1 can be calculated on the basis of the relationship between the opposite end deflection angle θ1 and the load P illustrated in FIG. 12. A result obtained according to such calculation is illustrated in FIG. 14.

Figure 15:
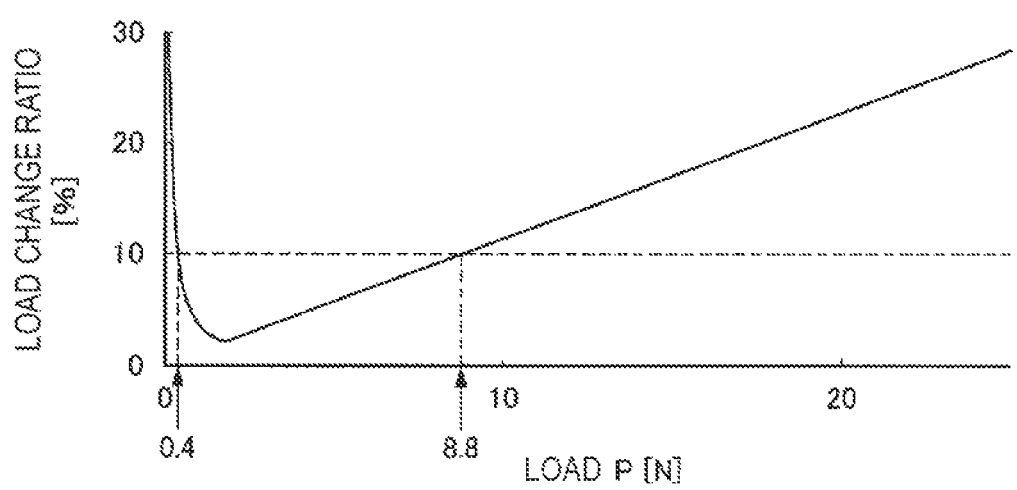
FIG. 15 is an explanatory diagram illustrating an example of a relationship between a load P applied to the leaf spring and a load change ratio.

FIG. 15 is an explanatory diagram illustrating an example of the relationship between the load P applied to the leaf spring 910 and a load change ratio. The load change ratio regarding each load P can be calculated on the basis of the relationship between the opposite end deflection angle θ1 and the load P illustrated in FIG. 12. A result obtained according to such calculation is illustrated in FIG. 15.

In the system illustrated in FIGS. 4 and 8, in the case where the load P is smaller than or equal to 1.85 [N], the part of the one end 910a side of the leaf spring 910 does not abut on the outer peripheral surface of the deformation guide 920. Accordingly, the part of the one end 910a side of the leaf spring 910 is not supported by the deformation guide 920. In the case where the load P is relatively small, that makes it possible to secure the state in which the rigidity of the leaf spring 910 is low. FIG. 13 illustrates that, in the case where the opposite end deflection angle θ1 having a correlation with the load P is relatively small, the rigidity of the leaf spring 910 is relatively low.

Here, as the rigidity of the leaf spring 910 is lower, the load change ratio is lower. In the system illustrated in FIGS. 4 and 8, in the case where the load P and the opposite end deflection angle θ1 are relatively small, the rigidity of the leaf spring 910 is lower. Accordingly, the load change ratio is relatively low. FIG. 14 illustrates that, in the case where the opposite end deflection angle θ1 having a correlation with the load P is relatively small, the load change ratio is relatively low. In addition. FIG. 15 illustrates that, in the case where the load P is relatively small, the load change ratio is relatively low. Note that the load P at the time when the opposite end deflection angle θ1 is 0 [°] is 0 [N]. Accordingly, as illustrated in FIGS. 14 and 15, when the load P and the opposite end deflection angle θ1 have values near 0, the load change ratio can have a relatively large value.

In this way, in the case where the load P is relatively small, the load change ratio is relatively low. Therefore, it is possible to secure the state in which measurement accuracy in the case where a measurement value of the opposite end deflection angle θ1 as the displacement amount of the leaf spring 910 is used to measure the load P applied to the leaf spring 910 is high.

The mechanical characteristics of the leaf spring 910 illustrated in FIGS. 14 and 15 define the relationship between the load change ratio and the opposite end deflection angle θ1, and the relationship between the load change ratio and the load P, respectively. Specifically, according to FIG. 14, the range of the opposite end deflection angle θ1 corresponding to the range within which the load change ratio falls below 10% is a range of 1 [°] to 8.5 [°]. In addition, according to FIG. 15, the range of the load P corresponding to the range within which the load change ratio falls below 10% is a range of 0.4 [N] to 8.8 [N]. Here, the mechanical characteristics of the leaf spring 910 depend on the setting values of the specifications of the leaf spring 910. Therefore, setting the specifications of the leaf spring 910 as appropriate makes it possible to appropriately set the ranges of the opposite end deflection angle θ1 and the load P corresponding to the range of the load change ratio corresponding to desired measurement accuracy. In addition, the mechanical characteristics of the leaf spring 910 also depend on the cross-sectional shape of the deformation guide 920. Therefore, setting the cross-sectional shape of the deformation guide 920 as appropriate also makes it possible to appropriately set the mechanical characteristics of the leaf spring 910.

4. ACTUATOR ACCORDING TO EMBODIMENT OF THE PRESENT DISCLOSURE

Next, with reference to FIGS. 16 and 17, the actuator 320 according to an embodiment of the present disclosure will be described. The actuator 320 transmits torque input from the outside to a target object on the output side via a leaf spring 322. The actuator 320 can be used, for example, for the artificial leg 1 described with reference to FIGS. 2 and 3 as described above.

Figure 16:
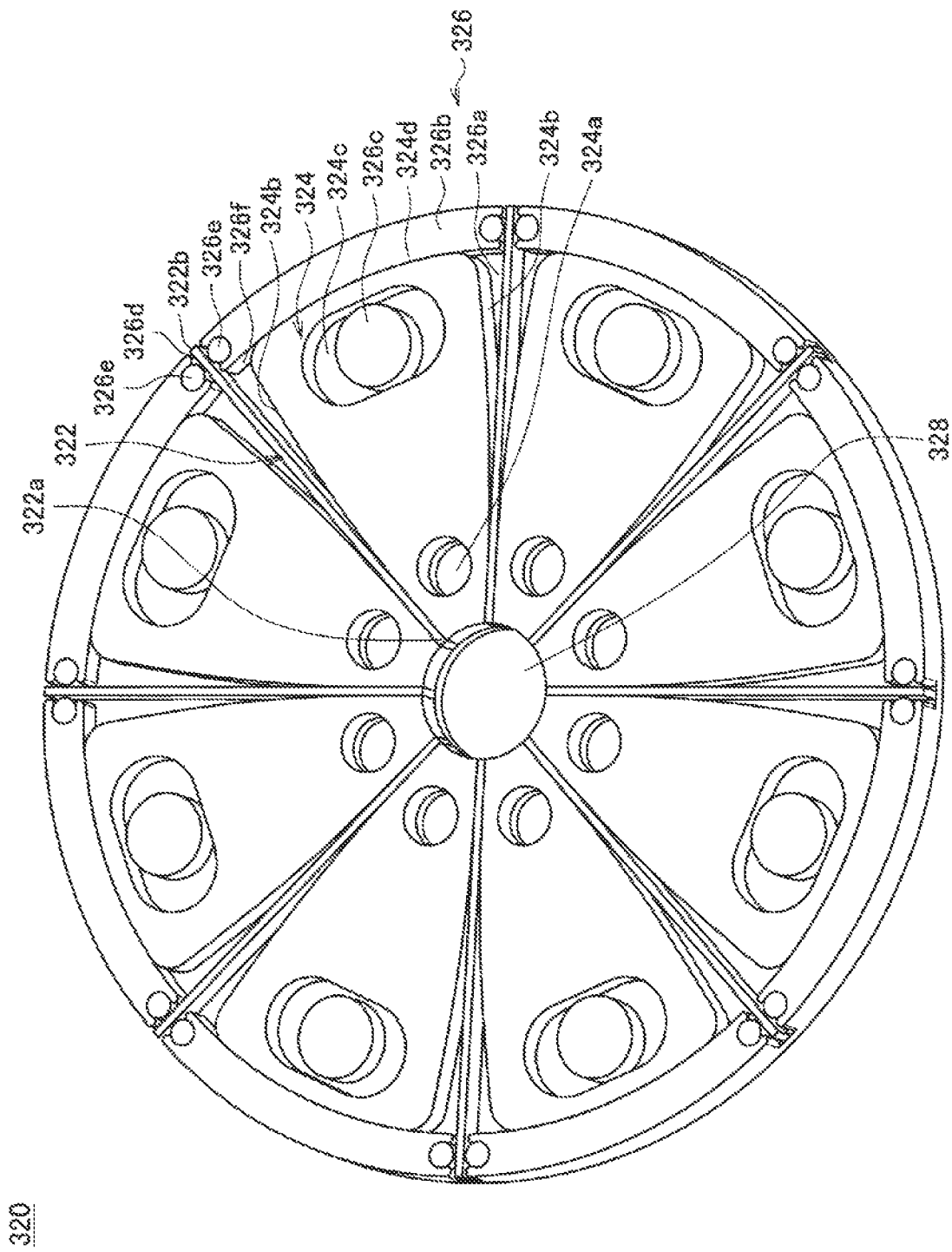
FIG. 16 is a schematic diagram illustrating an example of a configuration of an actuator according to an embodiment of the present disclosure.

FIG. 16 is a schematic diagram illustrating an example of the configuration of the actuator 320 according to the present embodiment. As illustrated in FIG. 16, the actuator 320 includes the leaf spring 322 that transmits torque, a support member 324 for supporting a part of the leaf spring 322, and a pivotal object 326 that is connected to a target object on the output side. FIG. 17 is a schematic diagram illustrating an example of a condition of the actuator 320 in the case where the one end 322a of the leaf spring 322 is relatively stopped with respect to the pivotal object 326 and in a case where the one end of the leaf spring pivots with respect to the pivotal object. As illustrated in FIG. 17, in the present embodiment, the one end 322a of the leaf spring 322 is configured to be relatively pivotable with respect to the pivotal object 326, thereby transmitting torque to the pivotal object 326 via the leaf spring 322.

The actuator 320 transmits, for example, torque output from the drive motor 340. Specifically, the torque output from the drive motor 340 is input into the leaf spring 322 of the actuator 320. Then, the torque is transmitted by the leaf spring 322 to the pivotal object 326. In this way, the leaf spring 322 transmits the torque output from the drive motor 340 to the pivotal object 326. The pivotal object 326 is connected to a target object on the output side, and can be configured such that the torque output from the actuator 320 is transmitted to the target object. More specifically, in the case where the actuator 320 is applied to the artificial leg 1 described with reference to FIGS. 2 and 3, the pivotal object 326 is provided to be pivotable in synchronization with the lower leg side member 200 serving as a target object on the output side. Therefore, the torque is transmitted to the pivotal object 326 via the leaf spring 322, thereby relatively pivoting the lower leg side member 200 with respect to the thigh side member 100.

The one end 322a of the leaf spring 322 is cantilevered. Specifically, the one end 322a of the leaf spring 322 is fixed to the output shaft 332 of the gear box 330 to be cantilevered. As illustrated in FIG. 16, the actuator 320 is, for example, substantially shaped like a disk, and the central part of the actuator 320 has a communication hole section 328 that communicates from one side to the opposite side along the central axis. The one end 322a of the leaf spring 322 is fixed to the output shaft 332, for example, in the state in which the output shaft 332 of the gear box 330 is inserted through the communication hole section 328. This allows the one end 322a of the leaf spring 322 to pivot in unison with the output shaft 332 of the gear box 330.

The rotary axis of the output shaft 332 of the gear box 330 may substantially agree with the central axis of the communication hole section 328. In that case, the one end 322a of the leaf spring 322 is pivotable on the central axis of the communication hole section 328. In addition, the output shaft 332 of the gear box 330 is pivotable in synchronization with the output shaft 342 of the drive motor 340. Therefore, the one end 322a of the leaf spring 322 is pivotable in synchronization with the output shaft 342 of the drive motor 340.

A plurality of the leaf springs 322 are provided, for example, along the pivotal direction of the one end 322a with intervals in between. Specifically, the eight leaf springs 322 are equidistantly provided along the pivotal direction of the one end 322a. More specifically, each of the eight leaf springs 322 extends along the radius direction of the communication hole section 328 as illustrated in FIG. 16. The eight leaf springs 322 are equidistantly provided along the circumferential direction. The leaf spring 322 is disposed such that the width direction of the leaf spring 322 substantially agrees with the axial direction of the communication hole section 328. In other words, the leaf spring 322 is disposed such that the plate thickness direction of the leaf spring 322 substantially agrees with the circumferential direction of the communication hole section 328.

The support member 324 is a member for supporting a part of the leaf spring 322. The support member 324 has, for example, a flat shape as illustrated in FIG. 16, and is disposed such that the width direction of the support member 324 substantially agrees with the plate thickness direction of the leaf spring 322. In addition, the plate thickness of the support member 324 may substantially agree with the width of the leaf spring 322. The support member 324 has a facing surface 324b that faces the leaf spring 322 in the plate thickness direction of the leaf spring 322. The facing surface 324b abuts on a part of the leaf spring 322 as described below in the case where torque transmitted by the leaf spring 322 is greater than a predetermined value.

A plurality of the support members 324 are provided, for example, along the pivotal direction of the one end 322a of the leaf spring 322 with intervals in between, and positioned between the two adjacent leaf springs 322 in the pivotal direction of the one end 322a. Specifically, in the actuator 320, as illustrated in FIG. 16, the leaf springs 322 and the support members 324 are alternately disposed along the circumferential direction of the actuator 320. The part of each of the leaf springs 322 and the support members 324 disposed in this way on the central side of the actuator 320 can form the communication hole section 328 as illustrated in FIG. 16.

The support member 324 and the one end 322a of the leaf spring 322 are each restricted in relative movement. Therefore, the support member 324 is pivotable in unison with the one end 322a of the leaf spring 322. Specifically, on the communication hole section 328 side of the support member 324, a through hole 324a for attaching the output shaft 332 of the gear box 330 to the actuator 320 is made. For example, a member such as a screw for connecting the output shaft 332 of the gear box 330 to the support member 324 can be inserted through the through hole 324a. The support member 324 and the one end 322a of the leaf spring 322 use the through hole 324a to be fixed to the output shaft 332 of the gear box 330.

The pivotal object 326 is relatively pivotable with respect to the one end 322a of the leaf spring 322. For example, as illustrated in FIG. 16, the pivotal object 326 includes a base section 326a that faces a plurality of the support members 324 in the plate thickness directions of the support members 324 and is shaped like an annular disk, and a projecting section 326b that is provided along the outer peripheral part of the base section 326a and projects onto the support member 324 side from the base section 326a.

The base section 326a is provided with a protruding section 326c at the position corresponding to each support member 324. The protruding section 326c protrudes onto the support member 324 side. The part of the outer peripheral side of each support member 324 in the actuator 320 has a through hole 324c that extends along the circumferential direction of the communication hole section 328. The protruding section 326c is inserted through the through hole 324c. The through hole 324c and the protruding section 326c can function as a guide that defines the pivotal direction of the pivotal object 326. In addition, a side surface 324d of each support member 324 on the outer peripheral side in the actuator 320 abuts on an inner peripheral surface 326f of the projecting section 326b. The side surface 324d of the support member 324 and the inner peripheral surface 326f of the projecting section 326b can also function as a guide that defines the pivotal direction of the pivotal object 326.

The pivotal direction of the pivotal object 326 may substantially agree with the circumferential direction of the communication hole section 328. In other words, the pivotal object 326 may be pivotable on the pivotal axis of the one end 322a of the leaf spring 322. That allows each member included in the actuator 320 to pivot on the common rotary axis. Accordingly, it is possible to miniaturize the actuator 320 more effectively.

The projecting section 326b has a groove section 326d at the position corresponding to each leaf spring 322 along the radius direction of the communication hole section 328. The groove section 326d has greater width than the plate thickness of the leaf spring 322. The part of the opposite end 322b side of the leaf spring 322 is inserted into the groove section 326d. Specifically, each surface of the groove section 326d facing the width direction is provided with a pin 326e that extends in the width direction of the leaf spring 322. The part of the opposite end 322b side of the leaf spring 322 is inserted between a pair of the pins 326e. That causes the pair of pins 326e to support the leaf spring 322 in the plate thickness direction. Therefore, the opposite end 322b of the leaf spring 322 is pivotable in unison with the pivotal object 326.

As described above, the leaf spring 322 transmits the torque output from the drive motor 340 to the pivotal object 326. In addition, the one end 322a of the leaf spring 322 is pivotable in synchronization with the output shaft 342 of the drive motor 340. In addition, the opposite end 322b of the leaf spring 322 is pivotable in unison with the pivotal object 326. In addition, the one end 322a of the leaf spring 322 is configured to be relatively pivotable with respect to the pivotal object 326. Therefore, in the case where torque is input from the drive motor 340 to the one end 322a of the leaf spring 322, as illustrated in FIG. 17, the one end 322a of the leaf spring 322 relatively pivots with respect to the opposite end 322b to cause the leaf spring 322 to perform deflection deformation in the plate thickness direction. Then, the load corresponding to the resilience of the leaf spring 322 is applied from the opposite end 322b of the leaf spring 322 to the pin 326e of the pivotal object 326. That transmits torque to the pivotal object 326 via the leaf spring 322. In this way, the leaf spring 322 transmits torque, so that the leaf spring 322 is capable of deflection deformation in the plate thickness direction in accordance with the torque.

Here, the one end 322a of the leaf spring 322 is cantilevered as described above. In addition, as illustrated in FIG. 17, in the case where the leaf spring 322 transmits torque to perform deflection deformation in the plate thickness direction in accordance with the torque, a reaction force F from the pin 326e of the pivotal object 326 is applied to the opposite end 322b of the leaf spring 322 in the plate thickness direction as a load. The reaction force F has the magnitude corresponding to the degree of deflection deformation of the leaf spring 322. Therefore, considering that the one end 322a of the leaf spring 322 is fixed, it is possible to consider the deformation of the leaf spring 322 similarly to the deformation of the leaf spring 910 at the time when the load P is applied in the plate thickness direction to the opposite end 910b of the leaf spring 910 whose one end 910a is cantilevered as described with reference to FIGS. 4 to 14. Note that the reaction force F as a load applied from the pin 326e of the pivotal object 326 to the opposite end 322b of the leaf spring 322 corresponds to the load P applied to the opposite end 910b of the leaf spring 910 described with reference to FIGS. 4 to 14. In addition, the reaction force F has correlation with torque transmitted by the leaf spring 322.

In the case where torque transmitted by the leaf spring 322 is greater than the predetermined value, the support member 324 according to the present embodiment supports a part of the leaf spring 322 on the deflection direction side. Specifically, in the case where the torque transmitted by the leaf spring 322 is greater than the predetermined value, the facing surface 324b of the support member 324 abuts on a part of the leaf spring 322. That causes a part of the leaf spring 322 to be supported by the support member 324 on the deflection direction side. The predetermined value can correspond to the value of the torque at the time when the bending moment imparted to the one end 322a of the leaf spring 322 reaches the bending moment corresponding to the predetermined allowable distortion corresponding to the upper limit value of distortion in an elasticity region of a material included in the leaf spring 322 in the process in which the transmitted torque is increased from a relatively small value.

Here, as described above, the support member 324 is pivotable in unison with the one end 322a of the leaf spring 322. Therefore, it is possible to consider the relationship between the support member 324 and the leaf spring 322 according to the present embodiment similarly to the relationship between the deformation guide 920 and the leaf spring 910 in the system described with reference to FIGS. 4 to 14. The support member 324 is provided, for example, close to the part of the one end 322a side of the leaf spring 322 in the plate thickness direction of the leaf spring 322. In the case where toque transmitted by the leaf spring 322 is greater than the predetermined value, the part of the one end 322a side of the leaf spring 322 may be supported on the deflection direction side.

In addition, the shape of the facing surface 324b may be set on the basis of the lower limit value ρmin of the curvature radius expressed with the formula (6). Specifically a cross-sectional curve in a cross section of the facing surface 324b orthogonal to the width direction of the leaf spring 322 may be an arc whose curvature radius is the lower limit value ρmin. In addition, a cross-sectional curve in a cross section of the facing surface 324b orthogonal to the width direction of the leaf spring 322 may be a part of the deflection curve of the leaf spring 322 on the one end 322a side in the case where the transmitted torque is the predetermined value. Note that the lower limit value ρmin can be calculated on the basis of the specifications of the leaf spring 322.

According to the present embodiment, providing the leaf spring 322 with the support member 324 causes a part of the leaf spring 322 to be supported by the support member 324 on the deflection direction side in the case where the torque transmitted by the leaf spring 322 is greater than the predetermined value. Even in the case where the transmitted torque exceeds the predetermined value, this makes it possible to prevent such deformation of the leaf spring 322 that the curvature radius is smaller than the lower limit value ρmin. In this way, in the case where the transmitted torque is relatively large, it is possible to secure the state in which the rigidity of the leaf spring 322 is high. Thus, it is possible to prevent plastic deformation from occurring in the leaf spring 322. Therefore, it is possible to miniaturize the actuator 320 while keeping the strength of the leaf spring 322. Therefore, it is possible to miniaturize the apparatus including the actuator 320.

In addition, according to the present embodiment, in the case where the torque transmitted by the leaf spring 322 is smaller than or equal to the predetermined value, a part of the leaf spring 322 does not abut on the facing surface 324b of the support member 324. Accordingly, the part of the leaf spring 322 is not supported by the support member 324. In the case where the transmitted torque is relatively small, that makes it possible to secure the state in which the rigidity of the leaf spring 322 is low. Here, as the rigidity of the leaf spring 322 is lower, a load change ratio indicating the degree of change in the reaction force F applied to the opposite end 322b in the case where the opposite end deflection angle θ1 fluctuates is lower. Therefore, in the case where the transmitted torque is relatively small, the load change ratio regarding the leaf spring 322 is relatively low.

Here, the displacement amount of the leaf spring 322 can be detected by the displacement sensor 350 as described above. Specifically, as the displacement amount of the leaf spring 322, the opposite end deflection angle θ1 that is a deflection angle at the opposite end 322b can be detected by the displacement sensor 350. Then, the reaction force F applied to the opposite end 322b of the leaf spring 322 can be calculated by the control apparatus 400 on the basis of the measurement value of the opposite end deflection angle θ1 corresponding to a detection result obtained by the displacement sensor 350. In addition, as the load change ratio is lower, the measurement accuracy is higher. Therefore, according to the present embodiment, in the case where the torque transmitted by the leaf spring 322 is relatively small, it is possible to secure the state in which the measurement accuracy is high in the case where the reaction force F applied to the opposite end 322b of the leaf spring 322 is measured.

In addition, the mechanical characteristics of the leaf spring 322 depend on the setting values of the specifications of the leaf spring 322. Specifically, the relationship between the load change ratio and the reaction force F, and the relationship between the load change ratio and the opposite end deflection angle θ1 in the leaf spring 322 depend on the setting values of the specifications of the leaf spring 322. Therefore, setting the specifications of the leaf spring 322 as appropriate makes it possible to appropriately set the ranges of the opposite end deflection angle θ1 and the reaction force F corresponding to the range of the load change ratio corresponding to desired measurement accuracy. Note that length l, plate thickness d, width w, Young's modulus E, the upper limit value εmax of distortion, and the safety factor n for the leaf spring 322 in the longitudinal direction can correspond to the specifications of the leaf spring 322. In addition, the mechanical characteristics of the leaf spring 322 also depend on the shape of the facing surface 324b of the support member 324. Therefore, setting the shape of the facing surface 324b of the support member 324 as appropriate also makes it possible to approximately set the mechanical characteristics of the leaf spring 322.

In addition, the actuator 320 includes the leaf spring 322, the support member 324, and the pivotal object 326, and has a relatively simple configuration. Therefore, it is possible to make the apparatus including the actuator 320 smaller and lighter more effectively.

The leaf spring 322 includes, for example, spring steel. In addition, the support member 324 and the pivotal object 326 may each include a resin. Specifically the support member 324 and the pivotal object 326 can each include nylon, polypropylene (PP), or the like. In this way, the support member 324 or the pivotal object 326 includes a resin, so that it is possible to make the apparatus lighter.

As described above, the plurality of leaf springs 322 are provided, for example, along the pivotal direction of the one end 322a with intervals in between. This makes it possible to reduce the bending moment imparted to each leaf spring 322 as compared with the case where the number of leaf springs 322 provided to the actuator 320 is one. Therefore, it is possible to more effectively prevent plastic deformation from occurring in the leaf spring 322. In addition, setting the number of leaf springs 322 provided to the actuator 320 as appropriate makes it possible to approximately set the mechanical characteristics of each leaf spring 322.

As described above, the plurality of support members 324 are provided, for example, along the pivotal direction of the one end 322a of the leaf spring 322 with intervals in between, and positioned between the two adjacent leaf springs 322 in the pivotal direction of the one end 322a. That allows the plurality of leaf springs 322 and the plurality of support members 324 to be configured to be symmetrical with respect to the plane including the rotary axes thereof. Therefore, even in the case where the direction of torque transmitted by the actuator 320 is reversed, the support of the leaf spring 322 by the support member 324 can attain operations and effects similar to those before the reversal.

5. CONCLUSION

According to an embodiment of the present disclosure as described above, the leaf spring 322 has the one end 322a cantilevered and transmits torque, so that the leaf spring 322 is capable of deflection deformation in the plate thickness direction in accordance with the torque. In addition, in the case where torque transmitted by the leaf spring 322 is greater than the predetermined value, the support member 324 supports a part of the leaf spring 322 on the deflection direction side. With this arrangement, in the case where the torque transmitted by the leaf spring 322 is greater than the predetermined value, a part of the leaf spring 322 is supported by the support member 324 on the deflection direction side. Therefore, in the case where the transmitted torque is relatively large, it is possible to secure the state in which the rigidity of the leaf spring 322 is high. Thus, it is possible to prevent plastic deformation from occurring in the leaf spring 322. Therefore, it is possible to miniaturize the actuator 320 while keeping the strength of the leaf spring 322. Therefore, it is possible to miniaturize the apparatus including the actuator 320.

In addition, according to the present embodiment, in the case where the torque transmitted by the leaf spring 322 is smaller than or equal to the predetermined value, a part of the leaf spring 322 does not abut on the facing surface 324b of the support member 324. Accordingly, the part of the leaf spring 322 is not supported by the support member 324. In the case where the transmitted torque is relatively small, that makes it possible to secure the state in which the rigidity of the leaf spring 322 is low. Therefore, in the case where the transmitted torque is relatively small, the load change ratio regarding the leaf spring 322 is relatively low. In addition, as the load change ratio is lower, the measurement accuracy in the case where the measurement value of the opposite end deflection angle θ1 as the displacement amount of the leaf spring 322 is used to measure the reaction force F applied to the opposite end 322b of the leaf spring 322 is higher. Therefore, according to the present embodiment, in the case where the torque transmitted by the leaf spring 322 is relatively small, it is possible to secure the state in which the measurement accuracy is high in the case where the reaction force F applied to the opposite end 322b of the leaf spring 322 is measured.

In addition, according to the present embodiment, the mechanical characteristics of the leaf spring 322 depend on the setting values of the specifications of the leaf spring 322. Therefore, setting the specifications of the leaf spring 322 as appropriate makes it possible to appropriately set the mechanical characteristics of the leaf spring 322.

Note that the above describes an example in which the support member 324 supports the part of the one end 322a side of the leaf spring 322 on the deflection direction side in the case where the torque transmitted by the leaf spring 322 is greater than the predetermined value. However, the part supported by the support member 324 in the leaf spring 322 is not limited to the example. For example, in the case where the torque transmitted by the leaf spring 322 is greater than the predetermined value, the part of the leaf spring 322 closer to the opposite end 322b side than the one end 322a may be supported by the support member 324. In addition, in the case where the torque transmitted by the leaf spring 322 is greater than the predetermined value, a plurality of parts of the leaf spring 322 may be supported by the support member 324.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present disclosure may also be configured as below.

(1)

An actuator including:

a leaf spring whose one end is cantilevered, the leaf spring being capable of deflection deformation in a plate thickness direction in accordance with torque by transmitting the torque; and a support member configured to support a part of the leaf spring on a deflection direction side in a case where the torque transmitted by the leaf spring is greater than a predetermined value.

(2)

The actuator according to (1), further including:

a pivotal object configured to be relatively pivotable with respect to the one end of the leaf spring, in which the leaf spring transmits torque output from a drive motor to the pivotal object.

the one end of the leaf spring is pivotable in synchronization with an output shaft of the drive motor, and an opposite end of the leaf spring is pivotable in unison with the pivotal object.

(3)

The actuator according to (2), in which the support member is pivotable in unison with the one end of the leaf spring.

(4)

The actuator according to (2) or (3), in which the pivotal object is pivotable on a pivotal axis of the one end of the leaf spring.

(5)

The actuator according to any one of (2) to (4), in which a plurality of the leaf springs are provided along a pivotal direction of the one end with an interval in between.

(6)

The actuator according to (5), in which the eight leaf springs are equidistantly provided along the pivotal direction of the one end.

(7)
  The actuator according to (5) or (6), in which
  a plurality of the support members are provided along the pivotal direction of the one end of the leaf spring with an interval in between, and positioned between the two adjacent leaf springs in the pivotal direction of the one end.
(8)
  The actuator according to any one of (1) to (7), in which the support member includes a resin.
(9)
  The actuator according to any one of (2) to (7), in which the pivotal object includes a resin.
(10)
  An artificial leg including:
  a thigh side member;
  a lower leg side member and
  an actuator configured to connect the thigh side member to the lower leg side member, and transmit torque to the lower leg side member to relatively pivot the lower leg side member with respect to the thigh side member, in which
    the actuator includes
    a leaf spring whose one end is cantilevered, the leaf spring being capable of deflection deformation in a plate thickness direction in accordance with torque by transmitting the torque, and
    a support member configured to support a part of the leaf spring on a deflection direction side in a case where the torque transmitted by the leaf spring is greater than a predetermined value.

REFERENCE SIGNS LIST 1 artificial leg
100 thigh side member
110 connection section
120 main body section
200 lower leg side member
210 extending section
220 ground contact section
320 actuator
322 leaf spring
322a one end
322b opposite end
324 support member
324a through hole
324b facing surface
324c through hole
324d side surface
326 pivotal object
326a base section
326b projecting section
326c protruding section
326d groove section
326e pin
326f inner peripheral surface
328 communication hole section
330 gear box
332 output shaft
340 drive motor
342 output shaft
350 displacement sensor
400 control apparatus
601 spring
601, 602 spring
602 spring
701 input side mass object
702 input side mass object
800 output side mass object
910 leaf spring
910a one end
910b opposite end
920 deformation guide

The invention claimed is:

1. An actuator comprising:
  a leaf spring having a first end that is cantilevered at a first point of the leaf spring, the leaf spring extending along a first direction to a second end that is free, the leaf spring being capable of deflection deformation along a second direction, different from the first direction, in accordance with torque applied to a first surface of the leaf spring at the second end, the leaf spring transmitting the torque; and
  a support member configured to support a part of the leaf spring on a second surface of the leaf spring, opposite the first surface, and on condition that the torque transmitted by the leaf spring is greater than a predetermined value, the support member contacts the second surface of the leaf spring such that the first end of the leaf spring is cantilevered at a second point of the leaf spring closer to the second end than the first point.

2. The actuator according to claim 1, further comprising:
  a pivotal object configured to be relatively pivotable with respect to the first end of the leaf spring, wherein
  the leaf spring transmits torque output from a drive motor to the pivotal object,
  the first end of the leaf spring is pivotable in synchronization with an output shaft of the drive motor, and
  the second end of the leaf spring is pivotable in unison with the pivotal object.

3. The actuator according to claim 2, wherein
  the support member is pivotable in unison with the first end of the leaf spring.

4. The actuator according to claim 2, wherein
  the pivotal object is pivotable on a pivotal axis of the first end of the leaf spring.

5. The actuator according to claim 2, wherein
  a plurality of leaf springs are provided along a pivotal direction of the first end with an interval in between.

6. The actuator according to claim 5, wherein
  the plurality of leaf springs are equidistantly provided along the pivotal direction of the first end.

7. The actuator according to claim 5, wherein
  a plurality of support members are provided along the pivotal direction of the first end of the leaf spring with an interval in between, and positioned between two adjacent leaf springs in the pivotal direction of the first end.

8. The actuator according to claim 2, wherein
  the pivotal object includes a resin.

9. The actuator according to claim 1, wherein
  the support member includes a resin.

10. The actuator according to claim 1, wherein a cross-sectional curve in a cross section of a surface of the support member facing the second surface of the leaf spring orthogonal to a width direction of the leaf spring has a curvature radius set at a lower limit of a curvature radius of the leaf spring.

* * * * *